(12) United States Patent
Malott et al.

(10) Patent No.: US 11,298,559 B2
(45) Date of Patent: *Apr. 12, 2022

(54) INDEPENDENT READINESS DETERMINATION FOR AUTOMATED EXTERNAL DEFIBRILLATOR DEPLOYMENT

(71) Applicant: Galibots Inc., Centennial, CO (US)

(72) Inventors: Charles L. Malott, Centennial, CO (US); Terence E. Lister, Fort Collins, CO (US); Charles Mansfield, Centerville, VA (US); Richard Mansfield, Arlington, VA (US); David Robertson, Fort Collins, CO (US)

(73) Assignee: Galibots Inc., Centennial, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/022,400

(22) Filed: Sep. 16, 2020

(65) Prior Publication Data

US 2020/0406047 A1    Dec. 31, 2020

Related U.S. Application Data

(63) Continuation-in-part of application No. 16/422,796, filed on May 24, 2019, now Pat. No. 10,806,939.

(51) Int. Cl.
*A61N 1/39* (2006.01)
*G08B 7/06* (2006.01)
(Continued)

(52) U.S. Cl.
CPC ......... *A61N 1/3925* (2013.01); *A61N 1/3904* (2017.08); *A61N 1/3993* (2013.01);
(Continued)

(58) Field of Classification Search
None
See application file for complete search history.

(56) References Cited

U.S. PATENT DOCUMENTS 9,858,783 B1 * 1/2018 Agrawal ............... H04W 4/021
10,806,939 B1 * 10/2020 Malott ................. A61N 1/3904
(Continued)

FOREIGN PATENT DOCUMENTS

JP      2004512909 A  *  4/2004  .......... A61N 1/3904
KR    20160085150 A  *  7/2016  .......... A61N 1/3925
(Continued)

*Primary Examiner* — Fekadeselassie Girma
(74) *Attorney, Agent, or Firm* — Kunzler Bean & Adamson

(57) ABSTRACT

An apparatus for independent readiness determination for AED deployment includes a controller configured to detect an AED enclosure event corresponding to one or more AEDs registered to be disposed within one or more corresponding AED enclosures, where the controller is configured to communicate data for classifying an AED enclosure event into a predetermined event category, and further includes a communication interface configured to communicate a response action in response to data of the AED enclosure event satisfying one or more predetermined criteria for the predetermined event category. A method and a computer program product also perform the functions of the apparatus.

20 Claims, 10 Drawing Sheets

(51) Int. Cl.
*G08B 21/18* (2006.01)
*H04W 76/10* (2018.01)
(52) U.S. Cl.
CPC .............. *G08B 7/06* (2013.01); *G08B 21/18* (2013.01); *H04W 76/10* (2018.02)

(56) References Cited

U.S. PATENT DOCUMENTS

| | | | | |
|---|---|---|---|---|
| 2002/0019747 | A1* | 2/2002 | Ware | G16H 10/20 705/2 |
| 2005/0069853 | A1* | 3/2005 | Tyson | G09B 7/00 434/247 |
| 2008/0318564 | A1* | 12/2008 | Kreiner | G08C 17/02 455/420 |
| 2008/0319768 | A1* | 12/2008 | Kreiner | G06Q 10/06 705/1.1 |
| 2009/0201147 | A1* | 8/2009 | Gottlieb | G08B 25/016 340/539.12 |
| 2010/0019921 | A1* | 1/2010 | Kreiner | G08B 25/14 340/4.3 |
| 2011/0172551 | A1* | 7/2011 | Al-Ali | A61B 5/6833 600/529 |
| 2012/0259378 | A1* | 10/2012 | Heinrichs | G01G 19/52 607/6 |
| 2015/0148855 | A1* | 5/2015 | Szakelyhidi | H01Q 1/2208 607/5 |
| 2017/0222303 | A1* | 8/2017 | Naidu | A61N 1/3904 |

FOREIGN PATENT DOCUMENTS

| | | | | |
|---|---|---|---|---|
| WO | WO-2005011249 | A1 * | 2/2005 | ......... A61N 1/37258 |
| WO | WO-2019068035 | A1 * | 4/2019 | ............. G16H 40/63 |

* cited by examiner

INDEPENDENT READINESS DETERMINATION FOR AUTOMATED EXTERNAL DEFIBRILLATOR DEPLOYMENT

CROSS-REFERENCES TO RELATED APPLICATIONS

This is a continuation-in-part application of and claims priority to U.S. patent application Ser. No. 16/422,796 entitled "INDEPENDENT READINESS DETERMINATION FOR AUTOMATED EXTERNAL DEFIBRILLATOR DEPLOYMENT" and filed on May 24, 2019, for Charles L. Malott et al., the entire contents of which is incorporated herein by reference for all purposes legally allowed.

FIELD

The subject matter disclosed herein relates to automated external defibrillator enclosure devices and more particularly relates to independent readiness determination for automated external defibrillator deployment.

BACKGROUND

Sudden Cardiac Arrests ("SCAs") which occur outside of a hospital account for hundreds of thousands of deaths annually in the United States alone. Even in cases in which SCA victims survive long enough to be admitted to a hospital, a significant percentage of SCA victims do not survive to hospital discharge, and of those who are discharged many suffer impaired neurological function.

Early defibrillation using an automated external defibrillator ("AED") is one of the best ways to improve SCA outcomes and save lives. However, installing an AED and hoping that a nearby responder will take appropriate action quickly enough to save the SCA victim's life fails to maximize the SCA victim's chances of survival.

Numerous models of AEDs exist which are manufactured by various manufacturers and have different features, different recommendations for storing to ensure that the AED is ready for use, different instructions, different interfaces, and so forth. Even though most AED manufacturers offer guidance for maintaining these in a ready to use state, some existing AEDs are stored in a way that fails to ensure that the AED itself is ready to be successfully used. Additionally, many potential responders are unaware of beneficial information that would help maximize the likelihood of successfully using an AED to respond to an SCA. Moreover, existing AED readiness recommendations and/or mechanisms fail to adequately address responder readiness.

SUMMARY

An apparatus for independent readiness determination for AED deployment is disclosed. A method and computer program product also perform the functions of the apparatus. One apparatus for independent readiness determination for AED deployment includes a controller configured to detect an AED enclosure event corresponding to an AED registered to be disposed within an AED enclosure, where the controller is configured to communicate data for classifying an AED enclosure event into a predetermined event category, and further includes a communication interface configured to communicate a response action in response to data of the AED enclosure event satisfying one or more predetermined criteria for the predetermined event category, where the communication interface is configured to periodically awaken and attempt to establish a wireless network connection for communicating AED enclosure event data using one or more credentials of a predetermined series of credentials selected from primary credentials, secondary credentials, and rescue credentials.

In various embodiments, the controller is configured to collect one or more AED readiness parameters selected from: an individual enclosure identifier for linking the AED enclosure to an individual AED identifier of the AED registered to be disposed within the AED enclosure; an enclosure access indicator that indicates whether the AED enclosure is open; an AED-presence indicator that indicates whether the AED is correctly disposed within the AED enclosure; an audible readiness indicator of the AED; a visual readiness indicator of the AED; and a storage environment indicator that measures a temperature, and/or a humidity within the AED enclosure.

In certain embodiments, the controller is configured to collect the one or more AED readiness parameters using one or more of: a sensor that is physically separate from and electrically unconnected to the AED; and a user interface of a mobile communication device. In some embodiments, the individual enclosure identifier is externally coupled to the AED enclosure and/or internally stored in a tangible memory. In some embodiments, the sensor is disposed inside the AED enclosure.

In various embodiments, the controller is configured to communicate with an access sensor configured to determine whether an access door of the AED enclosure is open. In one embodiment, the apparatus is configured to wake the controller from a dormant mode to an active mode in response to the access sensor determining that the access door is open. In various embodiments, the controller further communicates with an object sensor configured to determine whether the AED is disposed correctly within the AED enclosure. In certain embodiments, the object sensor includes a time-of-flight sensor configured to measure a reflected signal distance to determine whether the AED is correctly disposed within the AED enclosure.

In some embodiments, the controller communicates with an input transducer configured to collect audio data of the audible readiness indicator. In certain embodiments, the apparatus includes a filter that distinguishes the audible readiness indicator from sounds that fail to satisfy predetermined parameters for the audible readiness indicator. In various embodiments, the filter performs frequency domain processing and time domain processing on the audio data captured by the input transducer to distinguish the audible readiness indicator from the sounds that fail to satisfy the predetermined parameters for the audible readiness indicator. In one embodiment, the controller is part of a communication device external to the AED enclosure, where the communication device includes all a user interface configured to collect the one or more AED readiness parameters through the user interface.

A method for independent readiness determination for AED deployment is disclosed. In one embodiment, the method includes: initiating a request for a network connection between a plurality of stationary AED readiness apparatuses and a data network using one or more credentials selected from a predetermined series of credentials selected from primary credentials, secondary credentials, and rescue credentials for authenticating the plurality of stationary AED readiness apparatuses to the data network; and in response to establishing the network connection between the plurality of stationary AED readiness apparatuses and the data network: communicating event data for an automated external defibrillator ("AED") enclosure event the AED enclosure event corresponding to an AED registered to be disposed within an AED enclosure; classifying the AED enclosure event into a predetermined event category; and communicating a response action in response to the AED enclosure event.

In some embodiments, the event data includes user input data collected through a user interface and sensor data collected through one or more sensors that are physically separate from the AED and electrically unconnected to the AED, the method further comprising: performing a comparison of the user input data and the sensor data; and communicating results of the comparison to a mobile communication device, and/or to a second communication device. In various embodiments, the event data includes user input data collected through a user interface the method further including communicating the response action to facilitate configuration of the AED enclosure with an updated controller configured to collect the sensor data from at least one of the one or more sensors disposed within the AED enclosure.

In certain embodiments, the predetermined event category for the AED enclosure event is selected from an emergency response event, a maintenance event, and/or a fault event. In various embodiments, communicating the response action to the mobile communication device is performed in response to determining that the mobile communication device corresponds to a responder having a readiness status that satisfies one or more predetermined criteria for the predetermined event category. In some embodiments, the method further includes determining the readiness status of the responder based on a parameter selected from a level of training to respond to the AED enclosure event, a location of the mobile communication device corresponding to the responder, a user input indicating readiness of the responder, and/or an AED event response history of the responder.

A computer program product is disclosed that includes a computer program product comprising a non-transitory computer readable storage medium having program instructions embodied therewith, wherein the program instructions are executable by a mobile communication device to cause the mobile communication device to: configure a predetermined series of credentials selected from primary credentials and secondary credentials for attempting to connect a plurality of stationary AED readiness apparatuses to a data network; configure a mobile communication device as a temporary access point accessible using predetermined rescue credentials for one or more timed out AED readiness apparatuses to communicate one or more updated primary credentials and/or secondary credentials to the timed out AED readiness apparatuses; and in response to the AED readiness apparatus connecting to the data network: obtain event data for an automated external defibrillator ("AED") enclosure event detected by a detector controller, the AED enclosure event corresponding to an AED registered to be disposed within an AED enclosure; obtain responder data indicating a readiness status for a responder that is a user of the mobile communication device; and communicate a response action in response to classifying the AED enclosure event into a predetermined event category and determining that the readiness status for the responder satisfies predetermined criteria.

BRIEF DESCRIPTION OF THE DRAWINGS

A more particular description of the embodiments briefly described above will be rendered by reference to specific embodiments that are illustrated in the appended drawings. Understanding that these drawings depict only some embodiments and are not, therefore, to be considered to be limiting of scope, the embodiments will be described and explained with additional specificity and detail through the use of the accompanying drawings, in which.

DETAILED DESCRIPTION

Figure 1:
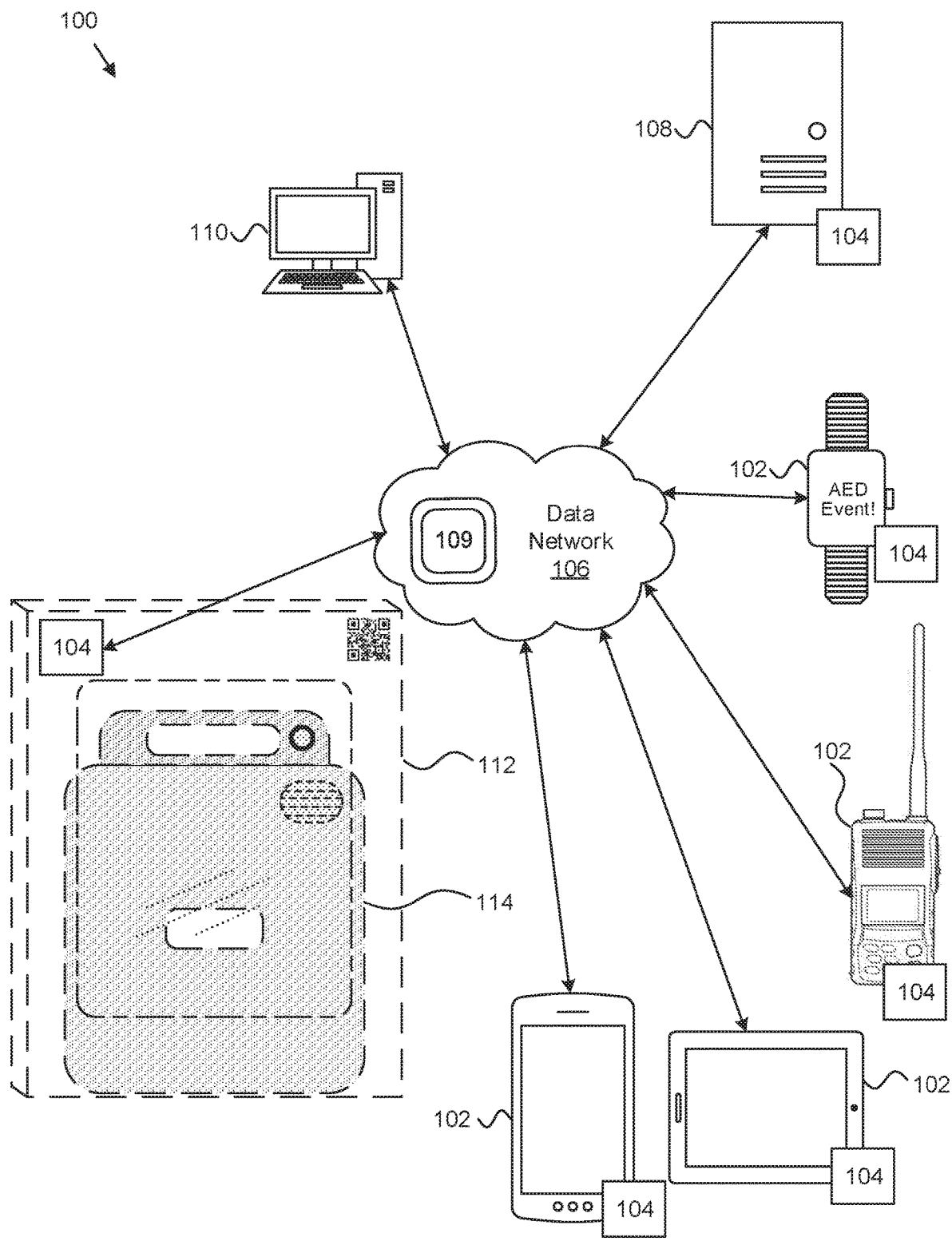
FIG. 1 is a schematic block diagram illustrating one embodiment of a system for independent readiness determination for AED deployment.

As will be appreciated by one skilled in the art, aspects of the embodiments may be embodied as a system, method, and/or program product. Accordingly, embodiments may take the form of an entirely hardware embodiment, an entirely software embodiment (including firmware, resident software, micro-code, etc.), or an embodiment combining software and hardware aspects that may all generally be referred to herein as a "circuit," "module," "component," "controller," "block," or "system." Furthermore, embodiments may take the form of a program product embodied in one or more computer readable storage devices storing machine-readable code, computer readable code, and/or program code, referred hereafter as code. The storage devices may be tangible, non-transitory, and/or non-transmission. The storage devices may not embody signals. In a certain embodiment, the storage devices only employ signals for accessing code.

Many of the functional units described in this specification have been labeled as modules, components, controllers, and blocks, to more particularly emphasize their implementation independence. For example, a module, component, controller, block, or system may be implemented as a hardware circuit comprising custom VLSI circuits or gate arrays, off-the-shelf semiconductors such as logic chips, transistors, or other discrete components. A module, component, controller, block, or system may also be implemented in programmable hardware devices such as field-programmable gate arrays, programmable array logic, programmable logic devices, or the like. Certain functional units described in the specification are specifically named and may be implemented using one or more modules, components, controllers, and blocks.

Modules, components, controllers, or blocks may also be implemented in code and/or software for execution by various types of processors. An identified module, controller, or block of code may, for instance, include one or more physical or logical blocks of executable code which may, for instance, be organized as an object, procedure, or function. Nevertheless, the executables of an identified module, controller, block, or system need not be physically located together but may include disparate instructions stored in different locations which, when joined logically together, include the module and achieve the stated purpose for the module, component, controller, or block.

Indeed, a module, component, controller, or block of code may be a single instruction, or many instructions, and may even be distributed over several different code segments, among different programs, and across several memory devices. Similarly, operational data may be identified and illustrated herein within modules, components, controllers, or blocks, and may be embodied in any suitable form and/organized within any suitable type of data structure. The operational data may be collected as a single data set or may be distributed over different locations including over different computer readable storage devices. Where a module, component, controller, or block, or portions thereof are implemented in software, the software portions are stored on one or more computer readable storage devices.

Any combination of one or more computer readable medium may be utilized. The computer readable medium may be a computer readable storage medium. The computer readable storage medium may be a storage device storing the code. The storage device may be, for example, but not limited to, an electronic, magnetic, optical, electromagnetic, infrared, holographic, micromechanical, or semiconductor system, apparatus, or device, or any suitable combination of the foregoing.

More specific examples (a non-exhaustive list) of the storage device would include the following: an electrical connection having one or more wires, a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Code for carrying out operations for embodiments may be written in any combination of one or more programming languages including an object-oriented programming language such as Python, Ruby, Java, Smalltalk, C++, or the like, and conventional procedural programming languages, such as the "C" programming language, or the like, and/or machine languages such as assembly languages. The code may execute entirely on a user's computer, partly on a user's computer, as a stand-alone software package, partly on a user's computer and partly on a remote computer, or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Reference throughout this specification to "one embodiment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment, but mean "one or more but not all embodiments" unless expressly specified otherwise. The terms "including," "comprising," "having," and variations thereof mean "including but not limited to," unless expressly specified otherwise. An enumerated listing of items does not imply that any or all of the items are mutually exclusive, unless expressly specified otherwise. The terms "a," "an," and "the" also refer to "one or more" unless expressly specified otherwise.

Furthermore, the described features, structures, or characteristics of the embodiments may be combined in any suitable manner. In the following description, numerous specific details are provided, such as examples of programming, software modules, components, controllers, or blocks, user selections, network transactions, database queries, database structures, hardware modules, components, controllers, or blocks, hardware circuits, hardware chips, etc., to provide a thorough understanding of embodiments. One skilled in the relevant art will recognize, however, that embodiments may be practiced without one or more of the specific details, or with other methods, components, materials, and so forth. In other instances, well-known structures, materials, or operations are not shown or described in detail to avoid obscuring aspects of an embodiment.

Aspects of the embodiments are described below with reference to schematic flowchart diagrams and/or schematic block diagrams of methods, apparatuses, systems, and program products according to embodiments. It will be understood that each block of the schematic flowchart diagrams and/or schematic block diagrams, and combinations of blocks in the schematic flowchart diagrams and/or schematic block diagrams, can be implemented by code. This code may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the schematic flowchart diagrams and/or schematic block diagrams block or blocks.

The code may also be stored in a storage device that can direct a computer, other programmable data processing apparatus, or other devices to function in a particular manner, such that the instructions stored in the storage device produce an article of manufacture including instructions which implement the function/act specified in the schematic flowchart diagrams and/or schematic block diagrams block or blocks.

The code may also be loaded onto a computer, another programmable data processing apparatus, or other devices to cause a series of operational steps to be performed on the computer, other programmable apparatus, or other devices to produce a computer implemented process such that the code, which executes on the computer or other programmable apparatus, provides processes for implementing the functions/acts specified in the flowchart and/or block diagram block or blocks.

The schematic flowchart diagrams and/or schematic block diagrams in the Figures illustrate the architecture, functionality, and operation of possible implementations of apparatuses, systems, methods, and program products according to various embodiments. In this regard, each block in the schematic flowchart diagrams and/or schematic block diagrams may represent a module, component, controller, block, segment, or portion of code, which includes one or more executable instructions of the code for implementing the specified logical function(s).

It should also be noted that, in some alternative implementations, the functions noted in the block diagram may occur out of the order noted in the Figures. For example, two blocks of a block diagram shown in succession may be executed substantially concurrently, or the blocks may sometimes be executed in the reverse order, depending upon the functionality involved. Other steps and methods may be conceived that are equivalent in function, logic, or effect to one or more blocks, or portions thereof, of the illustrated Figures.

Although various arrow types and line types may be employed in the flowchart and/or block diagrams, they are understood not to limit the scope of the corresponding embodiments. Indeed, some arrows or other connectors may be used to indicate only the logical flow of the depicted embodiment. For instance, an arrow may indicate a waiting or monitoring period of unspecified duration between enumerated steps of the depicted embodiment. It will also be noted that each block of the block diagrams and/or flowchart diagrams, and combinations of blocks in the block diagrams and/or flowchart diagrams, can be implemented by special purpose hardware-based systems that perform the specified functions or acts, or combinations of special purpose hardware and code.

The description of elements in each figure may refer to elements of proceeding figures. Like numbers refer to like elements in all figures, including alternate embodiments of like elements.

AEDs are becoming more and more ubiquitous in public places. Although AEDs are used infrequently, many sudden cardiac arrest emergencies occur in which the use of an AED is a matter of life or death. The time required to retrieve an AED and reach a victim of a sudden cardiac arrest dramatically affects the victim's chance of survival.

AED placement is a vital key in AED Program Implementation and providing the best chance of an SCA victim's survival. When a person goes into SCA, the chance of survival drops by 10% every 60 seconds that passes without defibrillation. As many as twenty percent of AEDs currently installed are not properly maintained and may not function when deployed in an emergency.

Some public places are encouraged or required to accept donations of automated external defibrillators in sufficient quantities to ensure reasonable availability for use during perceived sudden cardiac arrest emergencies. Yet, a significant number of AEDs installed in various places have expired pads, dead batteries, or are otherwise not operational.

In some instances, an AED is installed in a location but the readiness of the AED is not checked in accordance with a predetermined schedule. One possible option for trying to ensure the readiness of the AED is to pay a management service to physically check the AED periodically to make sure it is in good working order. At the same time, some persons at a particular location may be unaware of AED maintenance guidelines and/or regulations. Additionally, certain persons responsible for a particular location may have concerns about the expenses associated with paying an AED management service.

Another concern with certain AED installations is that sometimes, an AED is missing from a cabinet or other location where it is expected to be maintained. If an emergency occurs and a would-be responder attempts to obtain an AED from an expected location and discover that the AED is missing from the cabinet or other location where the AED is expected to be maintained, the potential rescue that could have been effectuated through the use of the AED is thwarted.

Another potential option for trying to ensure the readiness of an AED is to integrate circuitry and/or software into a newly developed AED to allow for electronic monitoring of the AED's readiness, through a wireless network. Yet, such an option does not address concerns about entering the readiness of existing AEDs that have already been installed/deployed in the field.

FIG. 1 is a schematic block diagram illustrating one embodiment of a system 100 for independent readiness determination for AED deployment. In one embodiment, the system 100 includes mobile communication devices 102, AED readiness apparatuses 104, data networks 106, servers 108, and remote communication devices 110. In one embodiment, the AED readiness apparatus 104 is disposed within an AED enclosure 112 that is configured to hold an AED 114. In some embodiments, at least a portion of the AED readiness apparatus 104 is implemented within one or more of the mobile communication devices 102. In certain embodiments, at least a portion of the AED readiness apparatus 104 is implemented in the server 108.

Even though a specific number of mobile communication devices 102, AED readiness apparatuses 104, data networks 106, servers 108, and remote communication devices 110 are depicted in FIG. 1, one of skill in the art will recognize that any number of mobile communication devices 102, AED readiness apparatuses 104, data networks 106, servers 108, and remote communication devices 110 may be included in the system 100.

In one embodiment, the term "mobile communication device" refers to one or more devices such as cellular phones, tablet computers, laptop computers, personal digital assistants ("PDA"s), tablet computers, multifunction vehicle consoles, smart watches, radios, streaming devices, or the like. In some embodiments, the mobile communication device 102 access the data network 106 directly using a network connection. In certain embodiments, the mobile communication device 102 may be one or more wearable devices such as smart watches, optical head-mounted displays, or the like.

In various embodiments, the AED readiness apparatus 104 is disposed within an AED enclosure 112 that is configured to hold an AED 114. In various embodiments, the AED enclosure 112 may be a hinged cabinet with the door, an open cabinet, a recessed cabinet, a rotating cabinet, a sleeve, a cupboard, a closet, or similar housing for an AED.

In one embodiment, the AED readiness apparatus 104 is configured to obtain event data for an AED enclosure event, where the AED enclosure event corresponds to the AED 114 registered to be disposed within the AED enclosure 112. In the embodiment, the AED readiness apparatus 104 is further configured to classify the AED enclosure event into a predetermined event category and to communicate a response action, in response to the AED enclosure event. In this manner, the AED readiness apparatus is used for providing independent readiness determination for automated external defibrillator deployment.

In certain embodiments, one or more of the mobile communication devices 102 includes an embodiment of the AED readiness apparatus 104. In some embodiments, one or more of the mobile communication devices 102 communicates with the AED readiness apparatus 104 over the data network 106. In various embodiments, at least a portion of the AED readiness apparatus 104 is implemented within the server 108. In some embodiments, the server communicates with one or more of the mobile communication devices 102 and/or with an embodiment of at least a portion of the AED readiness apparatus 104 disposed within the AED enclosure 112. Further details regarding the structures and functions of various embodiments of the AED readiness apparatus 104 are provided below with respect to FIGS. 2-7.

The data network 106, in one embodiment, includes a digital communication network that transmits digital communications. In some embodiments, the data network 106 includes a wireless network such as a narrow band wireless data network, wireless cellular network, local wireless network, such as a Wi-Fi network, a Bluetooth® network, a near field communication ("NFC") network, and ad hoc network (composed of individual devices communicating with each other directly), and/or the like. In certain embodiments, the data network 106 may include a wide area network ("WAN"), a storage area network ("SAN"), a local area network ("LAN"), an optical fiber network, the Internet, or another digital communication network.

The data network 106 may in some embodiments, include one or more servers 108, one or more access points 109, routers, switches, and/or other networking equipment. In certain embodiments, an AED readiness apparatus 104 disposed within an AED enclosure 112 is configured to periodically wake and connect to the data network 106 via the one or more access points 109. In some embodiments, the AED readiness apparatus 104 connects and authenticates to the data network 106 via the one or more access points 109. In certain embodiments, the data network 106 also includes computer readable storage media such as a hard disk drive, an optical drive, nonvolatile memory, RAM, or the like.

In one embodiment, the data network 106 includes two or more networks. In various embodiments, the data network 106 may include a radio network that transmits digital and/or analog signals. In certain embodiments, the data network 106 is a peer-to-peer network or an ad hoc network that may be formed between two or more radios, two or more cellular phones, and/or two or more vehicle communication devices. In some embodiments, the data network 106 includes satellite communications.

The server 108, in some embodiments, includes more than one server. In various embodiments, the server 108 includes web services, cloud services, backend services, and/or application programming interfaces ("APIs"), web APIs, and the like. In certain embodiments, the server 108 includes processing services, storage services, application-specific rules engines, and so forth.

In FIG. 1, the remote communication device 110 is depicted, in one embodiment, as a desktop personal computer ("PC"). In some embodiments, the remote communication device 110 may be a smart phone, a tablet computing device, a radio, a wearable computing device, a dispatch console, a vehicle computing device, or any similar communication device configured to communicate over the data network 106. In some embodiments, the remote communication device 110 is a mobile communication device 102.

In one embodiment, the remote communication device 110 is located off-premises (also sometimes called "off-premise") from the mobile communication device 102 and/or the AED readiness apparatus 104. In other embodiments, the remote communication device is located on the same premises (sometimes referred to as "on-premise") near the mobile communication device 102 and/or the AED readiness apparatus 104. In some embodiments, the term "remote communication device" refers to a communication device that communicates with the AED readiness apparatus 104 which is disposed within the AED enclosure 112. In other embodiments, the term "remote communications device" refers to a communication device that communicates with the AED readiness apparatus 104 which is implemented at least in part within the mobile communication device 102.

Figure 2:
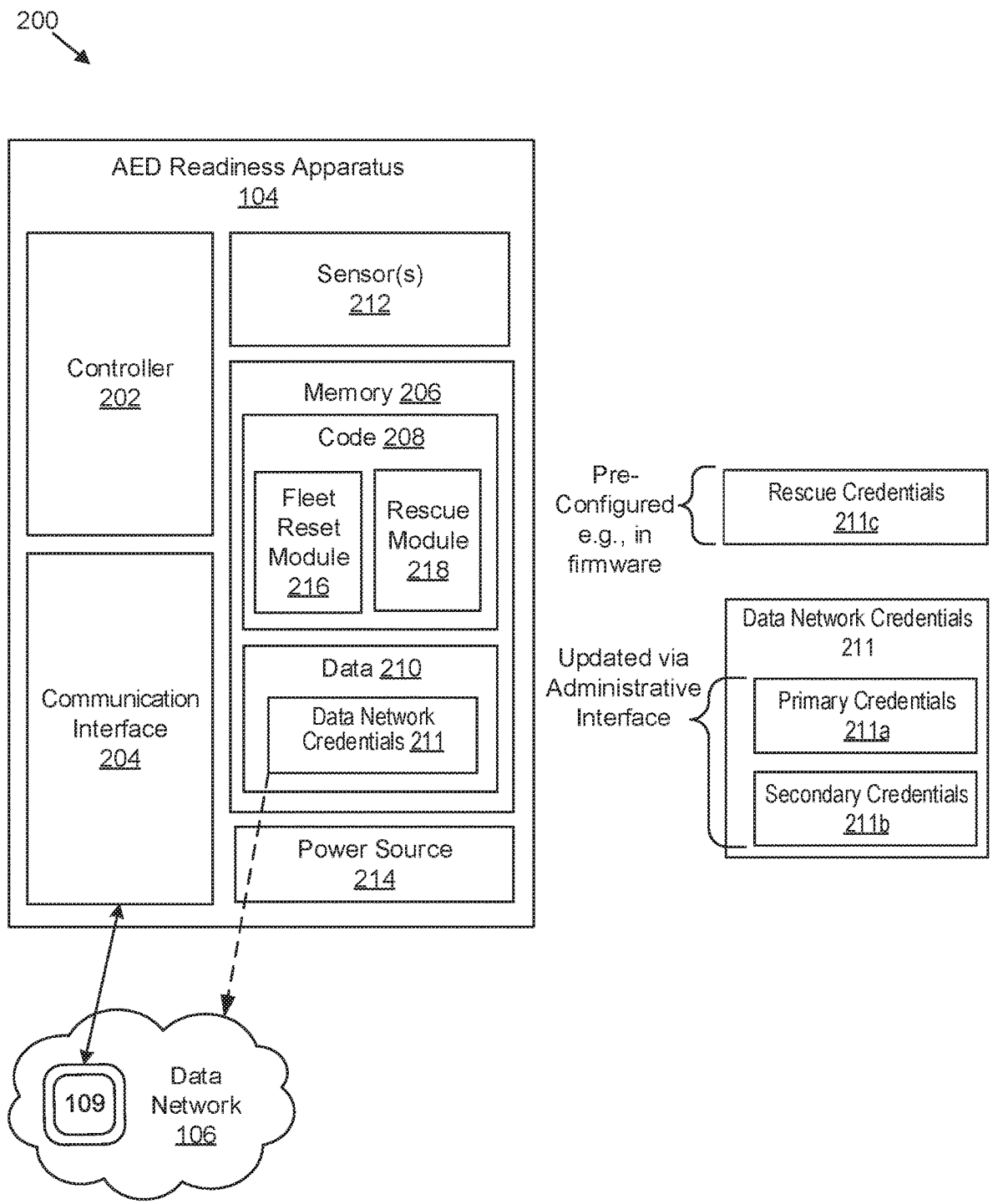
FIG. 2 is a schematic block diagram illustrating one embodiment of an apparatus for independent readiness determination for AED deployment.

FIG. 2 is a schematic block diagram illustrating one embodiment of an apparatus 200 that may be used for independent readiness determination for AED deployment. The apparatus 200 includes one embodiment of the AED readiness apparatus 104. In one embodiment, the AED readiness apparatus 104 includes a controller 202 configured to detect an AED enclosure event corresponding to an AED registered to be disposed within AED enclosure, where the controller 202 is configured to obtain AED enclosure event data for classification into a predetermined event category, and a communication interface 204 configured to communicate a response action in response to the AED enclosure event satisfying predetermined criteria for the predetermined event category. In some embodiments, the AED readiness apparatus 104 includes a power source 214. In various embodiments, the AED readiness apparatus 104 includes one or more sensors 212, a memory 206, code 208, and data 210 that may be stored with the memory 206.

In certain embodiments, the code 208 may include a fleet reset module 216 that is configured to enable one or more AED readiness apparatuses 104 to reset data network credentials 211 in response to a credential update command. In various embodiments, the code 208 may include a rescue module 218 that enabled the one or more AED readiness apparatuses 104 to periodically connect with the data network 106 to communicate data related to AED enclosure events to devices connected to the data In certain embodiments, the AED readiness apparatus 104 is configured to connect to the data network 106 using the data network credentials 211. In such embodiments, the data network credentials 211 may include one or more primary credentials 211a, one or more secondary credentials 211b, and rescue credentials 211c. In various embodiments, the data network credentials are used to authenticate the AED readiness apparatus 104 to the data network 106.

In certain embodiments, communicating the response action may include sending a message such as a text message, an application notification, an SMS, an audible tone, a recorded voice message, etc. For example, in one embodiment, the response action includes sending a message in response to detecting an AED enclosure event such as a maintenance event in which the controller 202 detects that pads of the AED have exceeded an expiration date. The message, in one embodiment, may be a text message or voice message indicating that the pads of the AED will soon be approaching the expiration date or have passed the expiration date. In some embodiments, the response action may be to automatically place an order for new pads based on a predetermined automatic order profile.

In various embodiments, the controller 202 is configured to communicate the AED enclosure event data to the server 108 which includes a rules engine that is configured to perform classification according to predetermined rules for different types of AED enclosure events. In various embodiments, the rules engine may be implemented using rule management system services on a server that provides the ability to register, define, classify, and manage all the rules used in classifying the AED enclosure events and communicating response actions to a communication device. The rule management system may further verify the consistency of rule definitions and the relationship between different roles as well as determining specific software components or applications that interact with one or more of the rules. In certain embodiments, the rules engine is implemented using database queries, statistical analysis, lookup tables, logical rule hierarchy, or similar algorithms. In certain embodiments, the rules engine performs one or more of the functions of the apparatuses 200, 300, 400, 500, and/or 600. In various embodiments, the rules engine performs algorithms that include one or more of the steps of the methods 800 and/or 900.

As used herein, the term "AED registered to be disposed within the AED enclosure" means that the AED 114 is assigned, logged, listed, recorded, enrolled, and/or similarly designated to be disposed within the AED enclosure.

In some embodiments, referred to herein as "stationary embodiments," the AED readiness apparatus 104 is configured to be disposed within an AED enclosure, such as, for example, the AED enclosure 112 depicted in FIG. 1. One example of a stationary embodiment is the AED readiness apparatus 304 depicted in FIG. 3 and described below in more detail with respect to FIG. 3. As used herein, the term "stationary" means configured to remain in a particular location during operation. At the same time, stationary embodiments (e.g., the AED readiness apparatus 304) may be installed, removed, transferred, or updated at various locations and within various AED enclosures 112.

In various stationary embodiments, the controller 202 is selected from any known controller capable of executing computer readable code 208 and/or capable of performing logical operations, such as, for example, a microcontroller, microprocessor, central processing unit ("CPU"), a field-programmable gate array ("FPGA"), or similar programmable controller. In some stationary embodiments, the controller 202 is communicatively coupled to the communication interface 204, a memory 206, sensors 212, and a power source 214.

In certain stationary embodiments, the communication interface 204 includes a wireless transceiver and/or wireless control circuitry that implement one or more of various wireless communications methods, such as, for example, a narrow band wireless, Wi-Fi, Bluetooth®, Bluetooth Low Energy ("BLE"), Near-field communication ("NFC"), Radio-frequency identification ("RFID"), Zigbee®, Z-wave®, 6LowPAN®, Thread®, Global System for Mobile communications ("GSM"), 3G/4G/5G/etc., wireless mobile telecommunications, SigFox®, Neul®, LoRaWAN®, sensor-specific wireless communications, and so forth. Such low power wireless communications provide communication of AED enclosure data while preserving battery of sensors or AED readiness apparatuses and components thereof. In certain stationary embodiments, the communication interface 204 includes more than one wireless transceiver and/or wireless control circuitry to implement more than one wireless communication method.

In other embodiments, referred to herein as "mobile embodiments," the AED readiness apparatus 104 is implemented in the mobile communication device 102. Examples of a mobile embodiment are the AED readiness apparatuses 404, 504, 604, depicted in FIGS. 4, 5, and 6 and described in more detail below with respect to FIGS. 4, 5, and 6. In certain mobile embodiments, the mobile communication device 102 in which the controller 202 and the communication interface 204 are implemented are external to the AED enclosure 112, but are configured to capture AED enclosure events including AED readiness indicators using a sensor 212 such as an optical sensor 418 and/or a user interface 420.

In various mobile embodiments, the controller 202 includes executable code 208 such as software modules, or blocks of code that are stored in a memory 206 of the mobile communication device and are executed by a processor of the mobile communication device, where the processor of the mobile communication device is communicatively coupled to the memory 206 of the mobile communication device, sensors 212, and the power source 214 of the mobile communication device.

In some mobile embodiments, the controller 202 of the AED readiness apparatus 104 may be configured to collect user input from a user interface of the mobile communication device 102. For example, a user of the mobile communication device 102 inputs data in response to questions 410 presented on the user interface such as, for example, "is the AED present within the AED enclosure?," "does a visual readiness indicator of the AED indicate that the AED is ready?," and/or "does an audible readiness indicator of the AED indicate that the AED is not ready?" such as, for example, emitting a beeping sound indicating that the battery of the AED needs to be replaced soon with the freshly charged battery.

The memory 206, in various stationary embodiments and mobile embodiments, is a computer readable storage medium. In some embodiments, the memory 206 includes volatile computer storage media. For example, the memory 206 may include a RAM, including dynamic RAM ("DRAM"), synchronous dynamic RAM ("SDRAM"), and/or static RAM ("SRAM"). In some embodiments, the memory 206 includes non-volatile computer storage media. For example, the memory 206 may include a hard disk drive, a flash memory, battery-backed SRAM, or any other suitable non-volatile computer storage device.

In certain embodiments, the memory 206 includes both volatile and non-volatile computer storage media. In some embodiments, the memory 206 stores code 208 and data relating to AED enclosure events and/or AED readiness. In some embodiments, the memory 206 also stores program code and related data, such as an operating system or other controller algorithms performed by the controller 202 in certain stationary embodiments or various mobile embodiments, performed by a processor of the mobile communication device.

Figure 3:
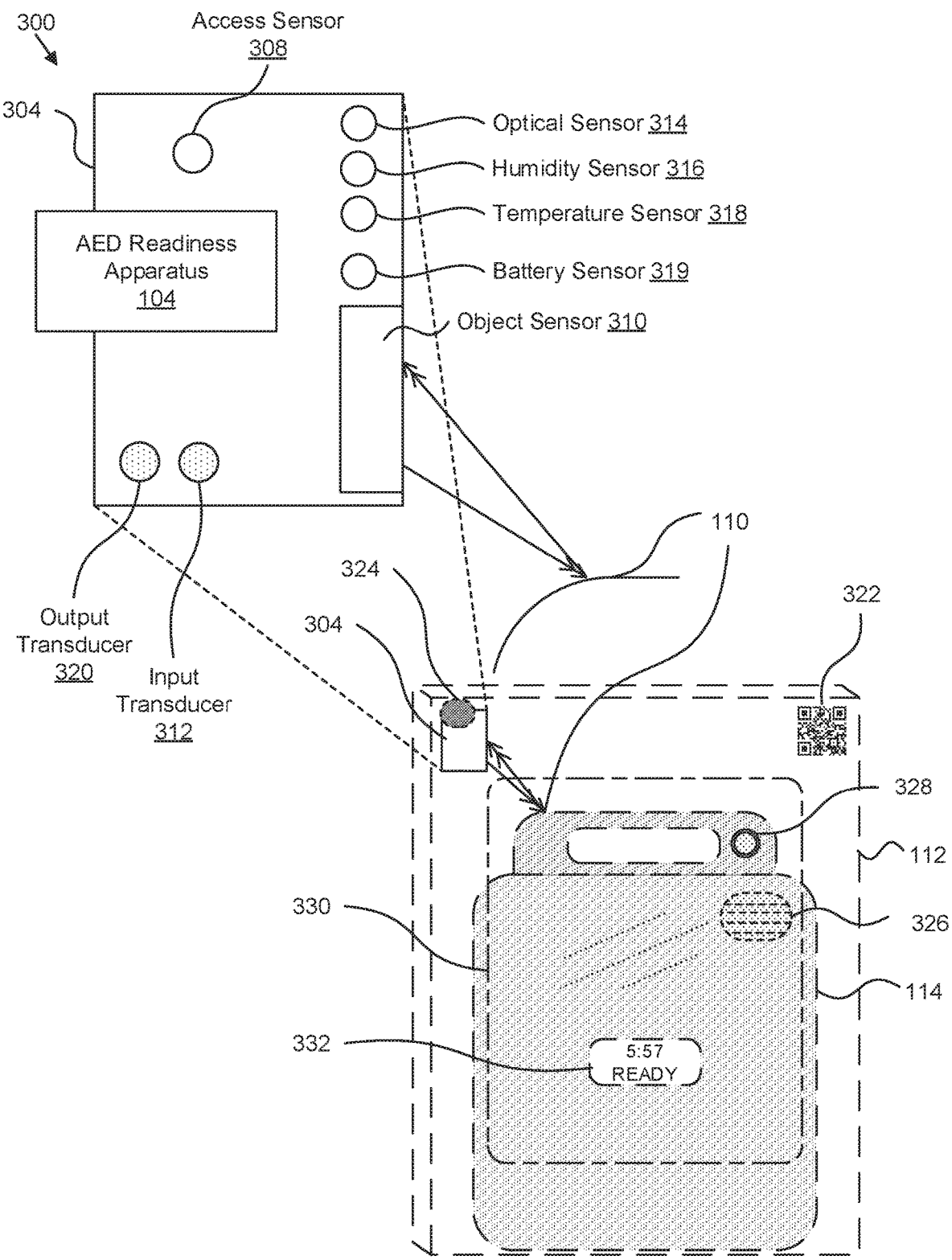
FIG. 3 is a schematic block diagram illustrating a stationary embodiment of an apparatus for independent readiness determination for AED deployment.

In various stationary embodiments, at least a portion of the sensors 212 are configured to be disposed within an AED enclosure such as the AED enclosure 112 depicted in FIG. 1 and FIG. 3. More details about the sensors 212 which are configured to be disposed within the AED enclosure are provided below with respect to FIG. 3.

In certain mobile embodiments, the sensors 212 may include a sensor such as an optical sensor, an RFID sensor, an NFC interface, a Bluetooth® interface, a Wi-Fi interface, or a similar device, implemented in the mobile communication device 102 for scanning, reading, writing, or and/or otherwise interacting with an AED identifier and/or an AED enclosure identifier. The sensors 212 in certain mobile embodiments further include wireless sensors disposed within the AED enclosure, where the wireless sensors are communicatively coupled to the controller 202 through the communication interface 204 to the processor of the mobile communication device 102.

The power source 214, in various stationary embodiments, includes a battery and/or circuitry for determining a status of the battery, such as, for example, voltage, operating current, remaining charge within the battery, and so forth. In certain mobile embodiments, the power source 214 includes multiple power sources such as the power source of the mobile communication device and/or a power source of any sensors 212 configured to be disposed within the AED enclosure 112. The power source 214 in various mobile embodiments includes circuitry, such as a battery sensor, for determining a status of the power source of the sensors 212 that are wireless such as, for example, voltage, operating current, remaining charge within a battery of the sensor, and so forth.

Figure 4:
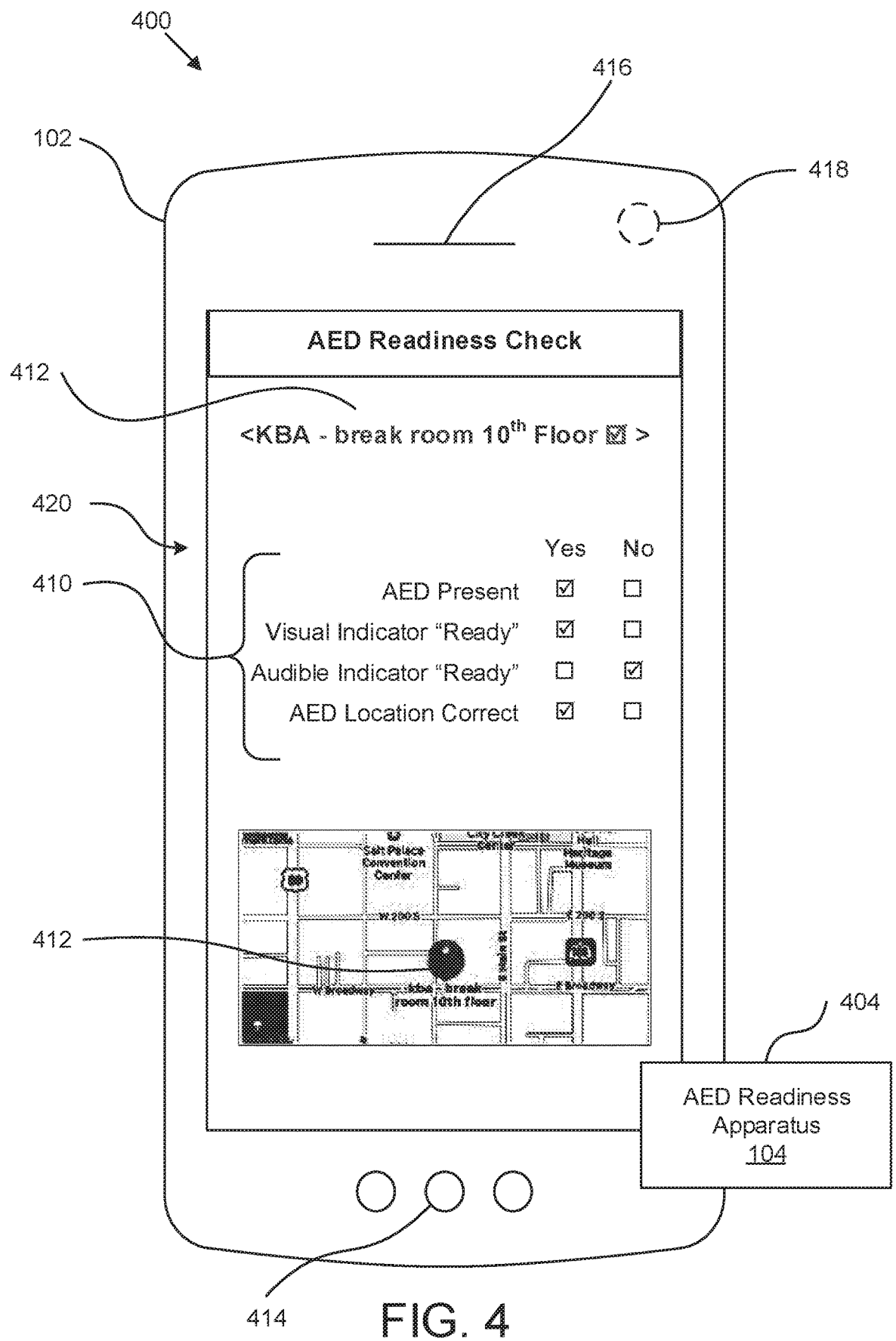
FIG. 4 is a schematic block diagram illustrating a mobile embodiment of an apparatus for independent readiness determination for AED deployment.

In one mobile embodiment of the AED readiness apparatus 104 (such as depicted in FIG. 4), a first instance of the AED readiness apparatus 104 is configured to determine whether the AED enclosure 112 includes a stationary embodiment of a second instance of the AED readiness apparatus 104 in which the controller 202 is disposed within the AED enclosure 112 (such as depicted in FIG. 3). In such an embodiment, the AED readiness apparatus 404 is configured to communicate a response action to facilitate configuration of the AED enclosure with an updated controller configured to collect the sensor data from at least one sensor 212 that is disposed within the AED enclosure. In one embodiment, the updated controller is implemented within an updated mobile embodiment to read sensor data from a sensor 212 that is a wireless sensor disposed within the AED enclosure 112. In another embodiment, the updated controller is implemented as a stationary embodiment of the AED readiness apparatus (e.g., 304) configured to be disposed within the AED enclosure 112.

In some embodiments, a mobile embodiment of the AED readiness apparatus 104 is configured to independently confirm that a stationary embodiment of the AED readiness apparatus 104 is operating correctly. In certain embodiments, AED enclosure event data is collected from more than one mobile embodiment of the AED readiness apparatus 104 and is aggregated. Further details regarding AED enclosure event data are described below with respect to the stationary embodiment of the AED readiness apparatus 304 depicted in FIG. 3 and the mobile embodiment of the AED readiness apparatus 404 depicted in FIG. 5.

FIG. 3 is a schematic block diagram illustrating a stationary embodiment of an apparatus 300 for independent readiness determination for AED deployment. In one embodiment, the AED readiness apparatus 304 is a stationary embodiment that includes an instance of the AED readiness apparatus 104 and is configured to be disposed within the AED enclosure 112. In one embodiment, the AED readiness apparatus 304 includes a controller 202, such as a processor as described above, and a communication interface 204 that includes a wireless transceiver and/or wireless control circuitry. In various embodiments, the AED readiness apparatus 304 includes the memory 206, the code 208, (including, for example, code for the controller 202, the communication interface 204, the sensors 212, the fleet reset module 216, and/or the rescue module 218), the data 210 (including, for example, the data network credentials 211), the sensors 212, and the power source 214, substantially as depicted in FIG. 2 and described above with respect to various stationary embodiments.

In various embodiments, the AED readiness apparatus 304 includes one or more sensors 212, such as for example, an access sensor 308, an object sensor 310, an input transducer 312, an optical sensor 314, a humidity sensor 316, and a temperature sensor 318 that are used to collect one or more AED readiness parameters. In some embodiments, the AED readiness apparatus 304 includes a battery sensor 319 that senses a status of a battery within the power source 214. In various embodiments, the AED readiness apparatus includes an output transducer 320.

In certain embodiments, the controller 202 is further configured to collect one or more AED readiness parameters such as an individual enclosure identifier, an individual AED identifier, an enclosure access indicator, an AED presence indicator that indicates whether the AED is presently disposed correctly within the AED enclosure, an audible readiness indicator of the AED, a visual readiness indicator of the AED, and a storage environment indicator that indicates a storage environment parameter such as temperature and/or humidity within the AED enclosure.

In one embodiment, the controller 202 is configured to collect the individual enclosure identifier and the individual AED identifier of the AED registered to be disposed within the AED enclosure using a sensor and/or a user interface of a mobile communication device 102. For example, when an AED is installed and/or registered to be disposed within a particular AED enclosure, in one embodiment, the controller collects the individual identifier using a sensor such as an optical sensor (e.g., a camera or bar code reader), an RFID reader, or another sensor, to collect the individual enclosure identifier and the individual AED identifier of the AED. In some embodiments, the individual identifier is associated with a bar code, a QR code, an RFID tag, and/or a similar label scanned by the mobile communication device. In other embodiments, the controller 202 is configured to collect the individual enclosure identifier and the individual AED identifier of the AED using the user interface of the mobile communication device (e.g., by entering the individual identifiers using the user interface).

In various embodiments, the individual AED enclosure identifier and the individual AED identifier may be multi-dimensional data structures that include various fields such as names, geographic locations, and/or any combination of data fields. For example, where the individual enclosure identifier includes a geographic location, the controller 202 may collect the geographical location using a geolocation module of the mobile communication device. It may be noted that in both stationary embodiments and mobile embodiments, the controller 202 may be configured to collect the AED readiness parameters using the sensors 212 and/or using the mobile communication device's sensors and/or user interface.

In one embodiment, the controller 202 is configured to collect an enclosure access indicator that indicates whether the AED enclosure is open using the access sensor 308. In various embodiments, the access sensor 308 is selected from various types of sensors and/or switches such as pushbutton switches, optical sensors, magnetic sensors, and the like. In certain embodiments, the AED readiness apparatus 304 is configured to wake the controller 202 from a dormant mode to an active mode in response to the access sensor 308 determining that the access door is open. For example, in one embodiment, the access sensor 308 is configured to be normally open (i.e., electrically disconnected) if the AED enclosure is closed and closed if the AED enclosure is open. If the enclosure door is closed, an electrical path through the access sensor 308 is open so that power from the power source 214 is beneficially conserved to prolong battery life. In response to the AED enclosure being opened, the electrical path through the access sensor 308 closes, thus waking the controller 202 from a dormant mode to an active mode. In various embodiments, multiple levels of power control may be configured for optimization of power usage under predetermined circumstances.

For example, in one embodiment the access sensor 308 includes a magnetic switch/sensor that is normally open if proximate to a magnetic field and closed if moved away from the magnetic field. In certain embodiments, a magnet 324 is coupled to an interior surface of an enclosure door of the AED enclosure 112 to move in or out of proximity with the access sensor 308 in response to the enclosure door closing or opening. In addition to the low-power benefits of a normally-open magnetic switch, the magnetic switch has a higher mechanical reliability than certain mechanical switches which beneficially improves the reliability of the AED readiness apparatus 304 for independently determining the readiness of the AED 114 for deployment in a sudden cardiac arrest emergency, thus improving the ability to save lives.

In one embodiment, the controller is configured to collect the AED-presence indicator that indicates whether the AED 114 is presently disposed correctly within the AED enclosure 112 using an object sensor 310. In various embodiments, object sensor 310 includes a time-of-flight sensor configured to measure a reflected signal distance to determine whether the AED 114 is disposed within the AED enclosure 112. For example, in one embodiment the object sensor 310 includes a laser-ranging sensor that measures a reflected signal distance to the AED 114. If the AED 114 is presently removed from the AED enclosure 112, the reflected signal has a longer time-of-flight than if the AED 114 is presently disposed within the AED enclosure 112.

In certain embodiments, the object sensor 310 senses a particular portion of the AED 114, such as, for example, a handle portion that is disposed nearer to a front surface of the AED 114. Accordingly, if the AED 114 is disposed backwards within the AED enclosure 112 so that a visual readiness indicator 328 (including, for example, a display 332) of the AED 114 are not visible through a window 330 of AED enclosure 112, the object sensor 310 determines that the AED 114 is positioned incorrectly within the AED enclosure 112. In various embodiments, the object sensor 310 uses infrared, ultrasonic, or any other type of electromagnetic signal to determine the reflected signal distance to the AED 114.

In some embodiments, the object sensor 310 includes any of several types of sensors, such as, for example, a strain gauge or any weight sensor that senses the weight of the AED 114 if presently disposed correctly within the AED enclosure 112. In other embodiments, the object sensor 310 includes a mechanical or optical switch that closes or opens a signal path used to determine whether the AED 114 is presently disposed correctly with the AED enclosure 112.

In one embodiment, the controller 202 is configured to collect an audible readiness indicator (e.g., a sound such as a beeping or chirping sound emitted by a buzzer, speaker, or transducer 326 of the AED 114) that indicates whether the AED 114 is ready for deployment. For example, an AED may be configured to emit an audible warning in response to a battery charge level being below a predetermined level, a pad electrode that has come unplugged, a failed self-test, and the like. In some embodiments, the controller 202 communicates with an input transducer 312 to capture audio data from the audible readiness indicator.

In some embodiments, the AED readiness apparatus 304 further includes a filter that distinguishes the audible readiness indicator from sounds that fail to satisfy predetermined parameters for the audible readiness indicator. In certain embodiments, the filter performs frequency domain processing and time domain processing on the audio data captured by the input transducer to distinguish the audible readiness indicator from the sounds that fail to satisfy the predetermined parameters for the audible readiness indicator.

As one example, in one embodiment, the AED 114 is configured to emit a beep sound having a particular tone or tones at specific intervals (e.g., 15 seconds, 90 seconds) in response to a battery level of the AED 114 having a charge level high enough to operate correctly but needing to be replaced within a predetermined period. Another AED from a different manufacturer may advise a user not to deploy an AED if it is emitting any type of tone. The AED 114 may also be configured to perform automatic self-tests at regular time intervals (e.g., daily, weekly, or monthly). In some embodiments, if the AED 114 detects an error, the transducer 326 is configured to emit a beep sound every 30 seconds. Thus, the filter of the AED readiness apparatus 304 is, in various embodiments, beneficially configured to distinguish different tones and/or patterns based on manufacturer specifications. Such manufacturer specifications are, in certain embodiments, configured to be accessed from the server 108 and to be updated from time to time.

Furthermore, certain other apparatuses in proximity to the AED 114 and/or the AED enclosure may also emit sounds such as beep sounds. For example, if the AED 114 is disposed near an entrance/exit detector or an elevator door that emits an audible readiness indicator, the filter may distinguish the tone or pattern of the AED audible readiness indicator from sounds emitted by the other apparatuses, thus reducing the likelihood of the AED readiness apparatus 304 communicating a response action base on a misidentified sound. In various embodiments, the filter of the AED readiness apparatus 304 utilizes Fast Fourier Transform technology to determine a tone of the audible readiness indicator.

In one embodiment, the controller 202 is configured to collect a visual readiness indicator of the AED 114 using a sensor 212 such as an optical sensor 314. For example, if the visual readiness indicator 328 of the AED 114 is communicated by emission or reflection of light having a predetermined color, brightness, and/or pattern, the optical sensor 314, in certain embodiments, detects the predetermined color, brightness, and/or pattern of the light. For example, in certain embodiments, the AED 114 includes a visual readiness indicator 328 that is configured to emit or reflect green light if the AED 114 is in a state of readiness and configured to emit or reflect red light if the AED 114 is not in a state of readiness. In some embodiments, the AED 114 is configured to emit the predetermined color of light using a predetermined pattern of blinks to attract attention.

In various embodiments, the optical sensor 314 is any of various technologies such as photodiode, phototransistor, cadmium sulfide cell, or similar technologies to detect the light. In some embodiments, the optical sensor 314 includes an array of optical detectors such as found in a digital imaging array and/or camera. In certain embodiments, the visual readiness indicator 328 of the AED 114 is communicated using an open pattern in response to the AED being in a state of readiness and an X-shaped or crossed-out pattern in response to the AED not being in a state of readiness. In some embodiments, the visual readiness indicator 328 includes the display 332 that displays a readiness status of the AED 114.

Exposure of an AED 114 to a temperature the exceeds or falls below a recommended temperature range is certain embodiments, affects battery life, and/or potentially operation of the AED 114. Similarly, exposure of the AED 114 to excessively humid environments also affects the battery life and/or potentially, the operation of the AED 114. In one embodiment, the controller 202 is configured to collect a storage environment indicator that indicates the temperature and/or the humidity of the environment within the AED enclosure 112 using a temperature sensor 318 and/or a humidity sensor 316. For example, the temperature sensor 318 includes one or more thermocouples, digital temperature sensors, or the like. In some embodiments, the temperature sensor 318 is integrated with the humidity sensor 316 into a single integrated circuit package.

In certain stationary embodiments, various of the sensors 212 (including the access sensor 308, an object sensor 310, an input transducer 312, an optical sensor 314, a humidity sensor 316, and a temperature sensor 318), are disposed within the AED enclosure 112, thus offering a degree of protection from the elements and/or from electrical, mechanical, or human interference.

In some embodiments, including in certain mobile embodiments, various of the sensors 212 are implemented as wireless sensors that may be accessed by the controller 212 as implemented in the mobile communication device 102 using a wireless connection, such as Bluetooth, Wi-Fi, and/or various other types of wireless communications as described above with respect to the AED readiness apparatus 104 of FIG. 2.

In other embodiments, including various mobile embodiments, some of the sensors 212 such as the optical sensor 314 and/or the input transducer 312 are implemented within the mobile communication device 102. For example, the mobile communication device 102 may include an instance of the AED readiness apparatus 104 in which the controller 202 is implemented using code executed by a processor of the mobile communication device 102, where the mobile communication device 102 uses a microphone of the mobile communication device 102 to collect data being emitted by the AED 114. Similarly, in certain mobile embodiments in which the controller 202 is implemented in the mobile communication device 102, the controller 202 may use a camera of the mobile communication device together with color and/or pattern recognition software to distinguish the readiness status indicated by various visual readiness indicators of the AED 114.

FIG. 4 is a schematic block diagram illustrating a mobile embodiment of an apparatus 400 for independent readiness determination for AED deployment. In one embodiment, the apparatus 400 includes a mobile communication device 102 and an AED readiness apparatus 404 that includes one instance of an AED readiness apparatus 104 with a controller 202 and a communication interface 204. In various embodiments, the AED readiness apparatus 404 is a mobile embodiment meaning that the controller 202 and the communication interface 204 are implemented within the mobile communication device 102 which is external to the AED enclosure.

In some situations, the AED 114 is deployed in a location such as a shopping mall, and office, or school, where hundreds of people may walk by one or more AEDs 114 every day. In such situations, providing the AED readiness apparatus 404 as a mobile embodiment implemented in smart phones, smart watches, or other mobile communication devices, improves the accessibility and approachability of the AED 114 by the persons most likely to use them in a rescue (e.g., an SCA emergency). One method of improving accessibility and approachability of the AED 114 is to engage such persons in performing AED readiness checks using the user interface 420 of the mobile communication device 102 as depicted in FIG. 4. Accessibility is improved by increasing public awareness of the location of the AED in the public space and approachability is increased by increasing awareness within likely responders that the AED 114 is designed to be usable by a layperson to save a life.

In one embodiment, the controller 202 of the AED readiness apparatus 404 is implemented in the mobile communication device which includes a user interface 420 configured to collect the one or more AED readiness parameters through the user interface 420. of the mobile communication device 102. In the embodiment, the user interface 420 is a touchscreen display that is configured to display one or more questions to which a user of the mobile communication device responds by touching a predetermined button, checkbox, and/or another input mechanism of the user interface 420.

In certain embodiments, the controller 202 of the AED readiness apparatus 404 is configured to collect an AED enclosure identifier in response to a user of the mobile communication device 102 scanning a scannable representation of a portion of the AED enclosure identifier 322 such as a barcode, a QR code, an RFID tag, etc., which is attached to the AED enclosure 112 using, for example, the optical sensor e.g., a camera of the mobile communication device 102.

The controller 202 communicates the AED enclosure identifier to a database, such as a database stored in the server 108 so that data entered using the user interface 420 is identified as corresponding to the particular AED enclosure 112 and/or the AED 114 registered to be disposed within the AED enclosure 112.

The user interface 420 is beneficially configured to minimize the time needed to collect the user input. In certain embodiments, the user interface 420 is configured to recognize one-touch responses to readiness queries presented via the user interface 420.

In various embodiments, the user interface 420 displays a graphical representation of the AED 114 showing the location and appearance of the visual readiness indicator 328 corresponding to a particular model of the AED 114 which is registered to be disposed within the AED enclosure 112. Similarly, the user interface 420 in some embodiments emits a sound representative of the audible readiness indicator corresponding to the particular model of the AED 114 is configured to facilitate a user performing a readiness check to recognize a predetermined audible readiness indicator.

In some embodiments, the user interface displays a query requesting a user of the AED readiness apparatus 404 to determine where the user interface whether the AED location 412 shown on a map and/or displayed textually is correct.

In various embodiments, the controller 202 is configured to perform a comparison of user input data collected through the user interface 420 and sensor data collected by the controller 202 or by a second instance of the controller 202 implemented within a stationary embodiment (e.g., as depicted in FIG. 3 with respect to the AED readiness apparatus 304) in which at least one of the sensors 212 is disposed within the AED enclosure 112 and/or a mobile embodiment (e.g., as depicted in FIG. 4 with respect to the AED readiness apparatus 404) which at least one of the sensors to 12 is disposed within the AED enclosure 112 and the controller is implemented within the mobile communication device 102 where the communication interface 204 of the AED readiness apparatus communicates via wireless communication with at least one of the sensors 212. In various such embodiments, the controller 202 is further configured to communicate results of the comparison to a mobile communication device 102 and/or to a second communication device such as the remote communication device 110 which may be a computer, a dispatch console, a mobile communication device, or any communication device configured to receive communications over the data network 106.

In some embodiments, the user input data and/or the sensor data are aggregated to provide aggregate results and/or statistical results for a particular group, location, AED model, AED make, user profile, sensor type, or any predetermined grouping of user input data and/or sensor data. Various such embodiments improve AED readiness checking technology by providing multiple independent sources of AED readiness data for various predetermined groupings.

In certain embodiments, the controller 202 is configured to collect user input data through the user interface 420 of the mobile communication device 102 and is further configured to communicate the response action to facilitate configuration of the AED enclosure with an updated instance of the controller 202 configured to collect the sensor data from at least one of the one or more sensors 212 disposed within the AED enclosure. For example, in one mobile embodiment, the AED readiness apparatus 404 scans a barcode, QR code, RFID tag, and/or similar individual AED enclosure identifier 322 and determines based that the AED enclosure 112 is not yet configured to include an updated controller 202. In some embodiments, the term "updated controller" may refer to a controller 202 of a stationary embodiment, such as the AED readiness apparatus 304, where the controller 202 and/or certain of the sensors 212 are disposed within the AED enclosure 112. Various such embodiments improve AED readiness checking technology by enabling particular AED installations to change from not having any internal sensors and/or any internal controller disposed within the AED enclosure 112 to an updated controller 202 where at least a portion of the controller 202 includes hardware components disposed within the AED enclosure 112. In other embodiments, the term "updated controller" refers to a stationary embodiment of the controller 202 where at least a portion of hardware components of the controller 202 disposed within the AED enclosure 112 are updated to include new features, new sensors, and/or new software.

In other embodiments, the AED readiness apparatus 404 uses an output transducer 416 (e.g., a speaker) to play a tone and/or pattern representative of the audible readiness indicator of the AED 114. In some embodiments, the AED readiness apparatus 404 uses the output transducer 416 of the mobile communication device the input transducer 312 to present a voice query to the user and uses the input transducer 414 of the mobile communication device 102 to determine a voice response from the user of the mobile communication device 102 to the voice query.

To maximize the probability of a successful response to a sudden cardiac arrest emergency, in certain embodiments, it is beneficial to involve multiple responders so that a first person responding may deploy the AED, while a second person calls a public emergency response service (e.g., a 911 emergency response service in the U.S.) and a third person runs to meet the public emergency responders at an entrance to the building to quickly guide the public emergency responders to the location of the SCA emergency, and so forth. In some embodiments, the communication interface is configured to communicate response action comprising a list of emergency response assignments configured to be selected to be performed by individual responders. For example, such a list may include an assignment to deploy the AED, initiate a phone call to a public emergency response service, meet public emergency responders at the entrance, and so forth.

Additionally, the likelihood of a successful response to SCA emergency increases in various embodiments as more people become aware of the location of the AED 114, know how to determine whether the AED 114 is ready to be deployed, learn how to deploy the AED 114 in an SCA emergency, know how to administer cardiopulmonary resuscitation ("CPR"), and so forth. Thus, one benefit of the AED readiness apparatus 404 being implemented in the mobile communication device 102, is that by engaging various potential responders to perform AED readiness checks using the user interface 420, the readiness status of potential responders is maximized through increased awareness of the benefits of using the AED 114 as well as through increased awareness of how to deploy the AED 114 and to deploy other potential responders to the same SCA emergency to perform other roles during the SCA emergency. In some embodiments, the roles are predetermined by responders or users configuring profiles that designate certain roles that the users are ready to fulfill. In other embodiments, the roles are determined based on the readiness status of various responders to respond to an AED enclosure event of a particular predetermined category.

Figure 5:
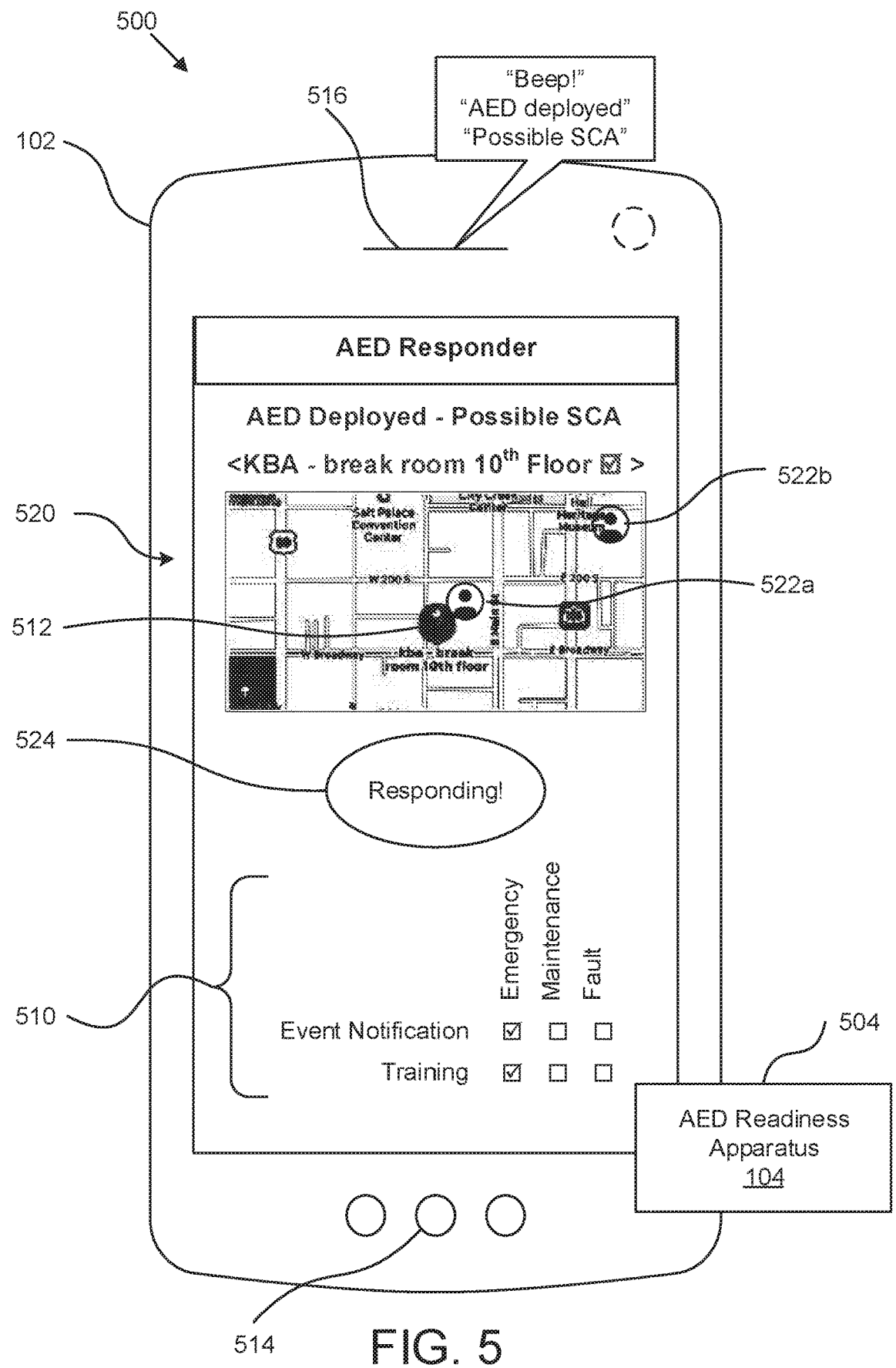
FIG. 5 is a schematic block diagram illustrating one embodiment of an apparatus for communicating a response action for an AED enclosure event.

FIG. 5 is a schematic block diagram illustrating one embodiment of an apparatus 500 for communicating a response action for an AED enclosure event. In one embodiment, the apparatus 500 includes an AED readiness apparatus 504 for independent readiness determination for AED deployment.

In one embodiment, the AED readiness apparatus 504 includes an instance of an AED readiness apparatus 104 that is implemented at least in part, in the mobile communication device 102. In other embodiments, the AED readiness apparatus 504 includes an instance of an AED readiness apparatus 104 is implemented at least in part as a stationary apparatus that accesses sensors 212 disposed within the AED enclosure 112 substantially as described above with respect to the AED readiness apparatus 304 depicted in FIG. 3.

Various AEDs are designed for use by persons with limited training. Similarly, certain AEDs are designed to provide audible or visual readiness indicators to persons who are aware that an AED is available and who know how to interpret the readiness indicators. The inventors of the subject matter disclosed herein have determined that use and/or maintenance of an AED is significantly improved by providing apparatuses and methods that are configured to determine the readiness of the AED itself and may also determine the readiness of responders to certain predetermined event categories relating to different types of AED enclosure events.

For example, in certain embodiments, a predetermined event category for an AED enclosure event is an emergency response event, a maintenance event, and/or a fault event. In various embodiments, an emergency response event is detected detecting a removal of the AED from the AED enclosure to rescue a person experiencing an SCA. In some embodiments, if the AED is not returned to its location within the AED enclosure within a predetermined time period, the controller 202 and/or the rules engine, presumes that the AED enclosure event is an AED emergency response event. A maintenance event, in various embodiments, includes any event related to maintaining the readiness of the AED such as, for example, battery power remaining, self-tests passed, and so forth and/or maintaining the readiness of consumables used in deployment of the AED such as, for example, pads, leads, instructions, and so forth.

In certain embodiments, a fault event indicates an event that is not classified as an emergency event or a maintenance event such as, for example, tampering with or inadvertently removing the AED from the enclosure. Other types of fault events might include for example spurious alarms or signals which go off at a time of day in which persons are unlikely to be occupying the premises where the AED enclosure is located. In some embodiments, a fault event is also classified as a maintenance event because certain repair and/or maintenance actions may be used to address the fault.

In various embodiments, the AED readiness apparatus 504 communicates data related to the readiness of a responder to respond to different types of AED enclosure events. In certain embodiments, a mobile communication device 102 may be used to help determine the readiness status of the responder based on a parameter such as a level of training to respond to one or more predetermined categories of AED enclosure events, a location of the mobile communication device corresponding to the responder, a user input indicating the readiness of the responder to respond to the relevant event, and/or an AED event response history of the responder.

For example, in certain embodiments, the AED readiness apparatus 504 may include a user interface 520 that collects user input 510 indicating the readiness status of the user to respond to a predetermined AED enclosure event for a predetermined event category. In some embodiments, user input 510 is collected to indicate certain event categories (e.g., emergency response, maintenance, and/or fault) for which the responder wants to receive event notifications. In one embodiment, the user input includes a one-touch user input (e.g., a user placing her thumb on a button or area of a touchscreen) on a user interface element such a button or even a touch within a certain area that a responder uses to indicate that the AED enclosure event is being responded to either by the responder using the apparatus 500 or by another responder. In certain embodiments, when a notification is sent to a responder regarding an emergency response event, a notification is also sent to remote communication devices letting them know which specific responders received the message have indicated that they are responding.

In various embodiments, the user input 510 includes audio (e.g. voice) data collected using a microphone of the mobile communication device 102. In some embodiments, a response action is communicated using a speaker 516 of the mobile communication device 102, such as, for example, by playing a beep tone, a voice recording, and/or a live voice providing the response action.

In some embodiments, the readiness status of the user to respond to the predetermined enclosure event for the predetermined event category is input directly by the user. In other embodiments, additional "responder readiness" data may be stored on the mobile communication device 102 or in the server 108 and may be manually and/or automatically updated from time to time. In certain embodiments, the AED readiness apparatus 504 compares the AED readiness status of the user to a predetermined criteria for the predetermined event category. For example, in response to an AED enclosure event that that is categorized within the predetermined event category of maintenance events, the response action communicated to the mobile communication device 102 is communicated to qualified maintenance personnel for a particular brand of AED, a certain AED service company with an agreement to service AEDs within a specified region, an on-site administrator responsible for AED maintenance, and so forth.

Similarly, in response to the controller 202 detecting AED enclosure event classified as an emergency response event, the AED readiness apparatus 504 communicates the response action to a communication device such as the mobile communication device 102 and/or the remote communication device where the communication device corresponds to a responder (e.g., a user to the communication device) having a readiness status that satisfies one or more predetermined event criteria for the emergency response event category. For example, in various embodiments the predetermined event criteria may include the readiness status of the responder such as being within 90 seconds of the AED enclosure, having completed training on AED use, having prior experience responding to emergency events.

In some embodiments, the predetermined event criteria may include the responder having a readiness status that is indirectly related to AED use such as, for example, the responder being certified to perform cardiopulmonary resuscitation ("CPR"), being assigned to direct public emergency responders to a location of the event, user input indicating readiness (e.g., opting in or agreeing to be an emergency responder for a particular AED location, organization, etc.).

In some embodiments, the AED enclosure event may be classified as a fault event. For example, referring to FIG. 3, if a person removes the AED 114 from the AED enclosure 112 mistakenly believing there is an emergency or being unaware that removal of AED 114 can trigger an AED enclosure event that is classified and communicated as an emergency event, the person may hear an audible signal from the AED readiness apparatus 304 such as an alarm-type sound emitted by the output transducer 320 and realize that the AED 114 should be put back in the AED enclosure 112. In response to the person putting the AED 114 back in the AED enclosure 112, the controller 202 may detect an AED event that is classified as a fault event and may in response communicate to public emergency responders that the previously communicated emergency event is no longer classified as an emergency and the public emergency responders do not need to respond. In some and embodiments, the term "satisfying the predetermined criteria" refers to readiness status data such as a readiness score exceeding a predetermined threshold, and/or falling within a predetermined range, and so forth. Such criteria or any criteria relevant to AED deployment may be input via the user interface of a mobile communication device or by a remote communication device such as an administrator application for an administrator of an AED fleet, a health office for school or business, or similar management or administrative role.

In certain embodiments, the AED readiness apparatus 504 is configured to cause a map showing a location of an AED 512 and locations of one or more responders 522a, 522b. In certain embodiments, the responder 522b may be outside a predetermined range such as within 90 seconds run/walk of the AED and still the communication interface 204 communicates a response action to the responder 522b. For example, at a large school or workplace, the responder 522b may be too remote from the location of the AED to respond directly within a 90 second time window. In some embodiments, if the responder is a health services manager or an organization administrator, the responder may configure the mobile communication device 102 to receive a communicated response action including AED enclosure event data for the event into a predetermined category, showing various responders who can respond more quickly, and so forth.

Figure 6A:
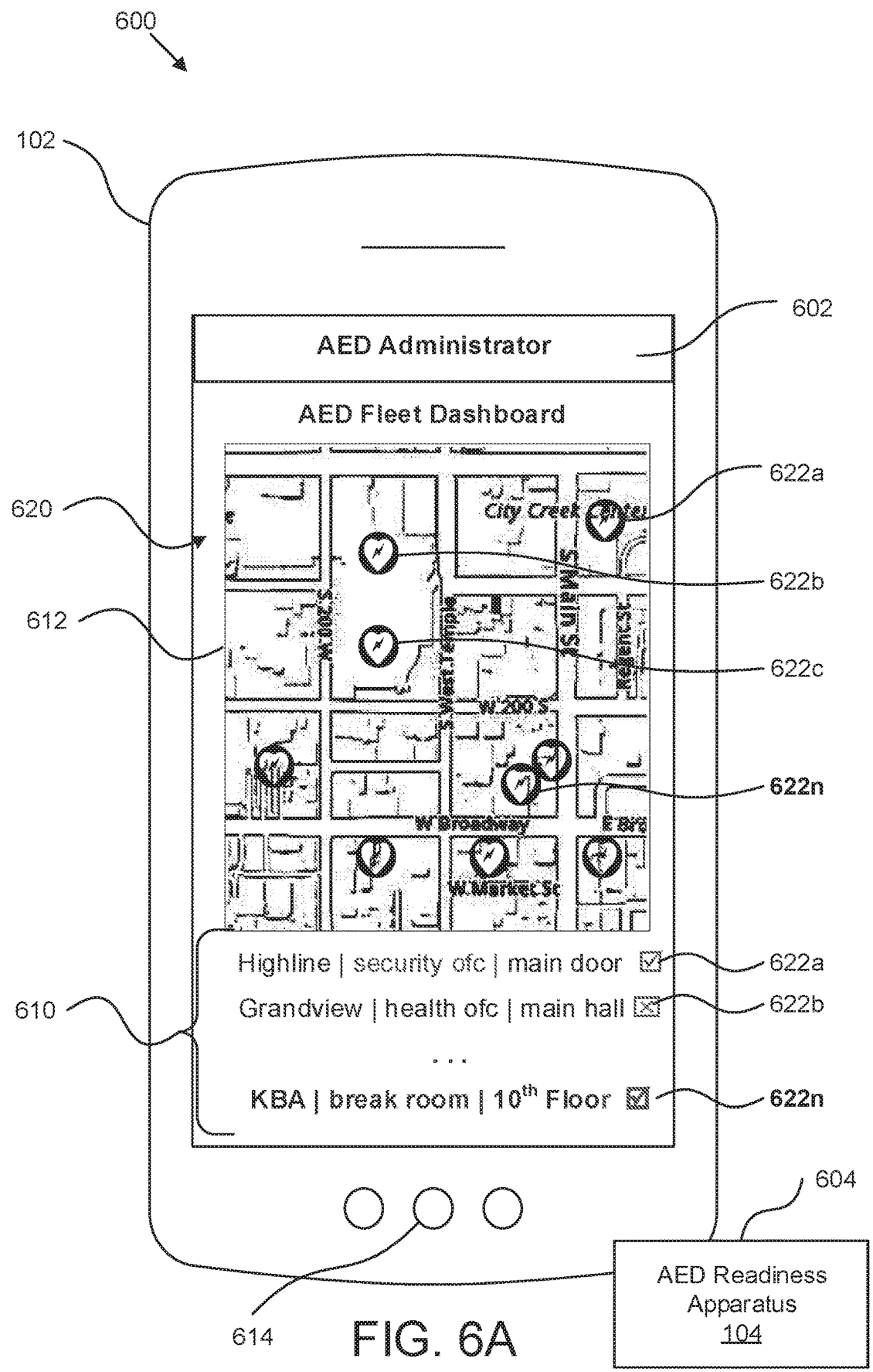
FIG. 6A is a schematic block diagram illustrating another embodiment of an apparatus for communicating a response action for an AED enclosure event.
Figure 6B:
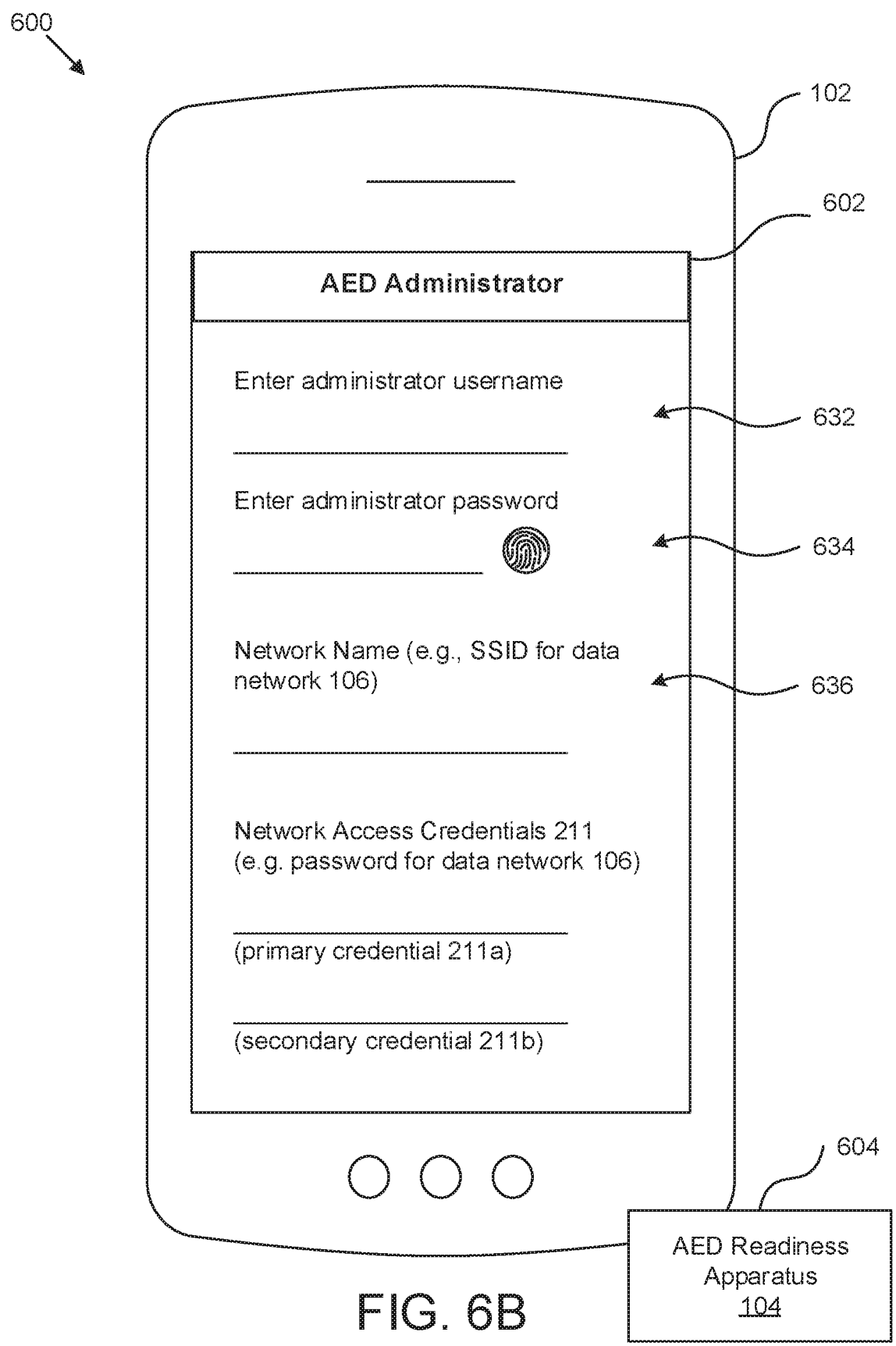
FIG. 6B depicts an administrative interface 600 for configuring access to the data network 106 and entering data network credentials 211.
Figure 7:
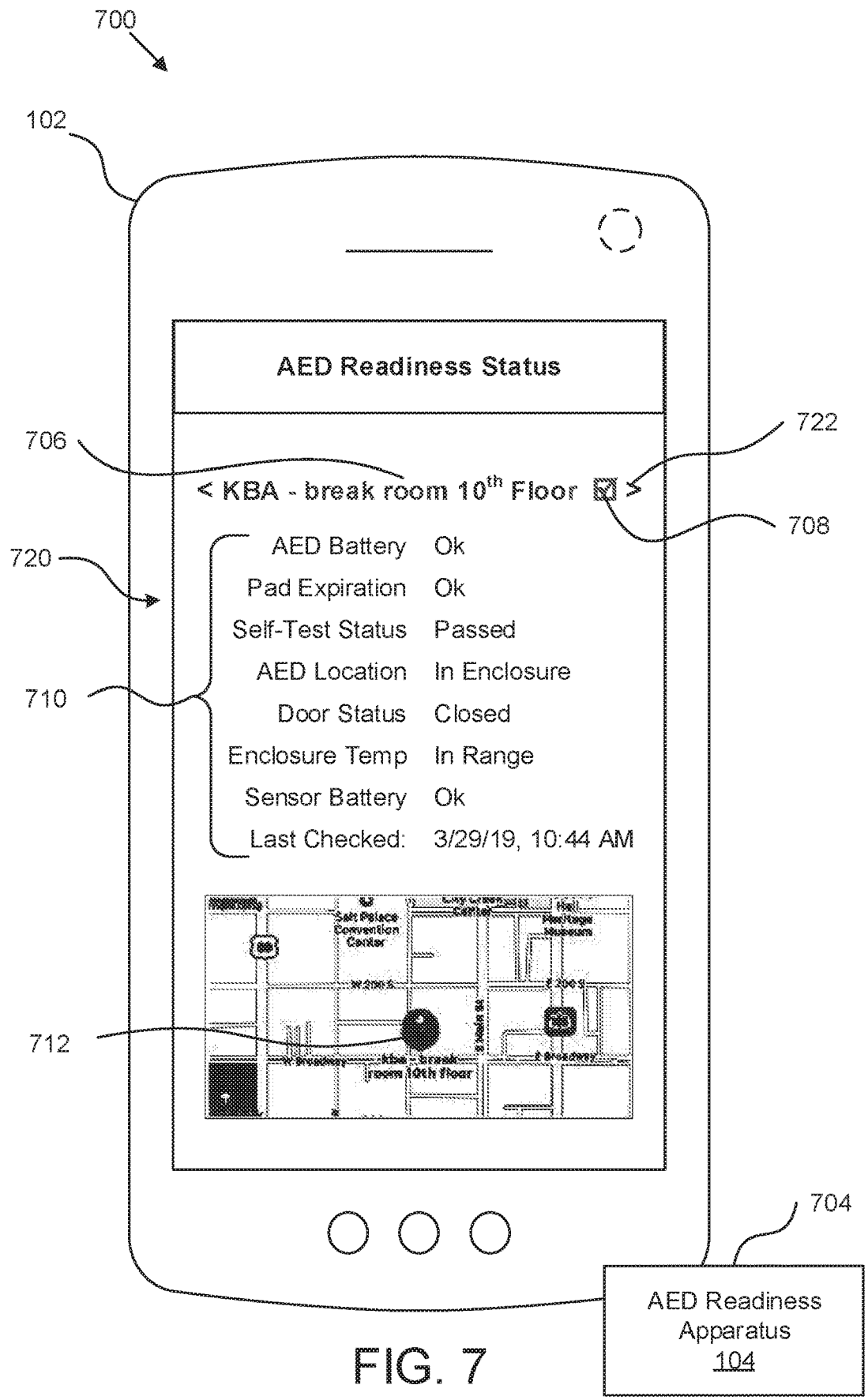
FIG. 7 is a schematic block diagram illustrating additional details of the embodiment of FIG. 6A.

Referring now to FIG. 6A, FIG. 6B, and FIG. 7 (with certain reference also to elements depicted and described above with respect to FIG. 1 and FIG. 2), FIG. 6A is a schematic block diagram illustrating one embodiment of an apparatus 600 for communicating a response action for an AED enclosure event for multiple AED enclosures. FIG. 6B depicts an administrative interface 600 for configuring access to the data network 106 and entering data network credentials 211. FIG. 7 is a schematic block diagram illustrating one embodiment of another apparatus 700 for communicating a response action for an AED enclosure event for an individual AED enclosure. In one embodiment, the apparatus 600 of FIG. 6 includes one instance of a mobile communication device 102 with an AED readiness apparatus 604 that includes one instance of an AED readiness apparatus 104 substantially as described above with respect to FIG. 2. In other embodiments, the apparatus 600 includes the mobile communication device 102 is configured to receive a communication from an AED readiness apparatus not implemented in the mobile communication device 102 such as, for example, the AED readiness apparatus 304 depicted in FIG. 3 or the AED readiness apparatus 404 depicted in FIG. 4.

In one embodiment as depicted in FIG. 6A, the apparatus 600 is configured to display a map 612 that displays a geographical location for multiple AED enclosures depicted as 622a, 622b, 622c . . . and 622n. In certain embodiments, the communication interface of the AED apparatus 604 or other the AED apparatuses 304, 404, and so forth, communicates a response action such as, for example, a readiness indicator for multiple AEDs e.g., 622a, 622b, 622c . . . and 622n. For example, in certain embodiments, the response action may cause an AED icon displayed on a user interface 620 to change colors from green to red in response to a controller 202 of the AED apparatus 604 (or of other the AED apparatuses 304, 404) detecting an AED enclosure event that is classified as an emergency response event, a maintenance event and/or a fault event, such as, for example, an emergency response event where the AED has been removed from the AED enclosure or maintenance event where the AED enclosure event is capable of potentially impairing the readiness of the AED to respond due to an issue with the AED itself and/or an issue with a consumable such as pads, wires, etc. In certain embodiments, textual information is display in a user input portion 510 where the records displayed correspond to AED enclosures 622a, 622b, 622c . . . 622n displayed on the map 612.

In other embodiments, the user interface 620 displays a dashboard that includes a list of selected AED enclosures, a description of the location, both at a high level such as a street address as well as at a more detailed level such as a particular area of a building, a particular room, or a particular floor of a multistory building. Such detailed information beneficially provides responders to emergency response events and maintenance events with graphical and/or textual information that facilitates a response action by a responder whose readiness status for a particular event category satisfies predetermined criteria.

In various embodiments, the user interface 620 displays textual representations which may like the map 612 be grouped hierarchically. For example, in some embodiments, groups of school districts are displayed at the highest level of hierarchy, then within a selected school district individual schools are displayed at a lower level of the hierarchy, and various rooms within the individual schools are displayed at a more detailed lower level of the hierarchy.

FIG. 6B depicts one embodiment of an apparatus 600 having an administrative interface 602 for configuring access to the data network 106 (depicted in FIG. 1) and entering data network credentials 211 depicted in FIG. 2. In certain venues, such as, for example, a business campus, an educational campus, a stadium, a convention center, and so forth, multiple AEDs may be deployed in an area serviced by a data network 106 with multiple access points through which an authenticated wireless device is provided access. To preserve battery life, in various embodiments, the AED readiness apparatus periodically connects and is authenticated to the data network 106 by providing recognized data network credentials 211.

Although FIG. 6B depicts the administrator interface 602 as being implemented in an application for a mobile communication device 102, in various embodiments, the administrator interface 602 may be implemented as a web-based service to be accessed for example by a web browser.

One of the challenges of deploying multiple AED readiness apparatuses 104 for an organization or venue with commonly shared network resources is updating the network credentials on all the devices when a change is made by the organization or venue. For example, in certain embodiments, an AED readiness apparatus such as the AED readiness apparatus 104 may use a venue-wide, business-wide, or educational campus-wide network access system that is protected and requires credentials such as a password to login to the network. Enabling multiple devices to access a particular network through multiple mesh access points makes it easier for mobile users to move about the campus while staying connected and without having to enter different passwords for each access point. It may be desirable for a venue, business, educational campus, or other organization to deploy multiple AED and multiple AED readiness apparatuses 104 that connect to a selected network using a particular password.

Furthermore, for security reasons, the administrator may from time to time update the password for accessing the selected network. In certain embodiments, the systems, apparatuses, and/or disclosed herein include a fleet reset module 216 that enables for an administrator to ensure that multiple AED readiness apparatuses can connect to the selected network using the new password without having to go to the location of each AED enclosure 112 to manually update the password.

In some embodiments, a user may use the administrative interface 602 to enter an administrator username 632 and administrator password 634 to be authorized to enter data such as data network credentials 211 for configuring the fleet reset module 216 included with certain embodiments of the AED readiness apparatus 104.

In various embodiments, the user may enter a network name 636 or SSID for accessing the data network 106. A user may enter or update network credentials 211, such as primary credentials 211a and/or secondary credentials 211b, which may be used by the fleet reset module 216 and/or the rescue module 218 of the AED readiness apparatus 104. The primary credentials 211a and the secondary credentials 211b enable a user to pre-configure one or more AED readiness apparatuses for an upcoming change in a network password, which in turn enables the AED readiness apparatuses to periodically sleep and wake up to preserve battery life even when a network password is changed before a wake-up procedure. Further details about the structures and functions of the fleet reset module 216 and the rescue module 218 are provided below with respect to FIG. 9.

FIG. 7 depicts an apparatus 700 configured to communicate more detailed readiness status information related to a particular AED enclosure and/or an AED registered to be disposed within the particular AED enclosure. In one embodiment, the apparatus 700 includes an AED readiness apparatus of 704 with one instance of an AED readiness apparatus 104 implemented for example as a mobile embodiment. In other embodiments, the apparatus 700 includes a mobile communication device 102 that receives information from any AED readiness apparatus, such as, for example, the AED readiness apparatus 304, 404, 504, 604, etc.

In certain embodiments, a user interface of the controller 202 of the apparatus 600 is configured to accept a user input such as, for example, a selection of a particular AED icon to display further details about the readiness status of an AED corresponding to the selected AED icon. In other words, in certain embodiments, FIG. 6 depicts an AED readiness dashboard at a high level or macrolevel showing multiple AED enclosures and FIG. 7 depicts an AED readiness dashboard or AED readiness status display at a detailed level or individual AED level for a particular AED enclosure.

In one embodiment, the apparatus 700 includes one instance of a mobile communication device 102 with an AED readiness apparatus 704 that includes one instance of an AED readiness apparatus 104 substantially as described above with respect to the apparatuses 200, 404, 504, and 604, depicted respectively in FIGS. 2, 4, 5, and 6. In other embodiments, the apparatus 700 communicates data collected by other AED apparatuses such as, for example, the stationary embodiment of the AED readiness apparatus 304 depicted in FIG. 3. In various embodiments, the apparatus 700 displays an AED enclosure identifier that includes a name, a general location, a detailed location, and/or and AED readiness indicator 714 for AED registered to be disposed with the selected AED enclosure. In various embodiments, a spin element 722 of the user interface 720 allows a different AED enclosure to be selected.

In various embodiments, the apparatus 700 displays AED readiness status data 710 relating to the readiness of an AED registered to be disposed within the selected AED enclosure, such as, for example, information related to an AED enclosure event that is classified as belonging to a maintenance event category. For example, in certain embodiments, the AED readiness status information includes data such as, for example, whether the AED battery has a charge level that satisfies one or more predetermined criteria for voltage or storage capacity to ensure that the AED will operate correctly and an AED emergency response event. The AED readiness status data 710 depicted also indicates whether the pad expiration date satisfies the predetermined criteria as to whether the pads are still within an acceptable range of dates prior to a predetermined expiration date.

The AED readiness status data 710 also includes, in certain embodiments, an indicator is whether a self-test performed by the AED passed or failed as detected by a beep code interpreted by a stationary embodiment of the AED readiness apparatus 304 or as recorded through user input to the user interface by a mobile embodiment of the AED readiness apparatus 404. In various embodiments, the AED readiness status data 710 further indicates whether the AED registered to be disposed within the location associated with the selected AED enclosure identifier 706 is present and correctly disposed within the AED enclosure as detected by a stationary embodiment of the AED readiness apparatus 104 such as depicted in FIG. 3 or a mobile embodiment of the AED readiness apparatus 104 such as depicted in FIG. 4.

Other AED readiness status data 710 depicted in one embodiment includes information about whether the cabinet or enclosure temperature is within an acceptable range and/or whether the sensor battery charge level meets the predetermined criteria for voltage and/or charge to ensure that the sensor battery is charged enough to operate correctly. In certain embodiments, the AED readiness status data 710 includes when the AED enclosure was last checked, either by a fixed embodiment and/or a mobile embodiment of the AED readiness apparatus 104. In certain embodiments, the apparatus 700 displays a map 712 showing the location of the selected AED enclosure.

The AED readiness apparatus 704 and/or any of the other AED readiness apparatuses 304, 404, 504, and 604, which communicate data for the apparatus 700 to display are configurable to display any relevant AED readiness status information and in certain embodiments, to display individual or aggregated data regarding the readiness status of various responders who have enrolled, subscribed, or otherwise opted in to receive response actions from the AED readiness apparatus corresponding to the selected AED enclosure. For example, at a school, a health services manager may use the apparatuses 600, 700 to display responder readiness data for multiple responders and/or individual responders respectively.

Figure 8:
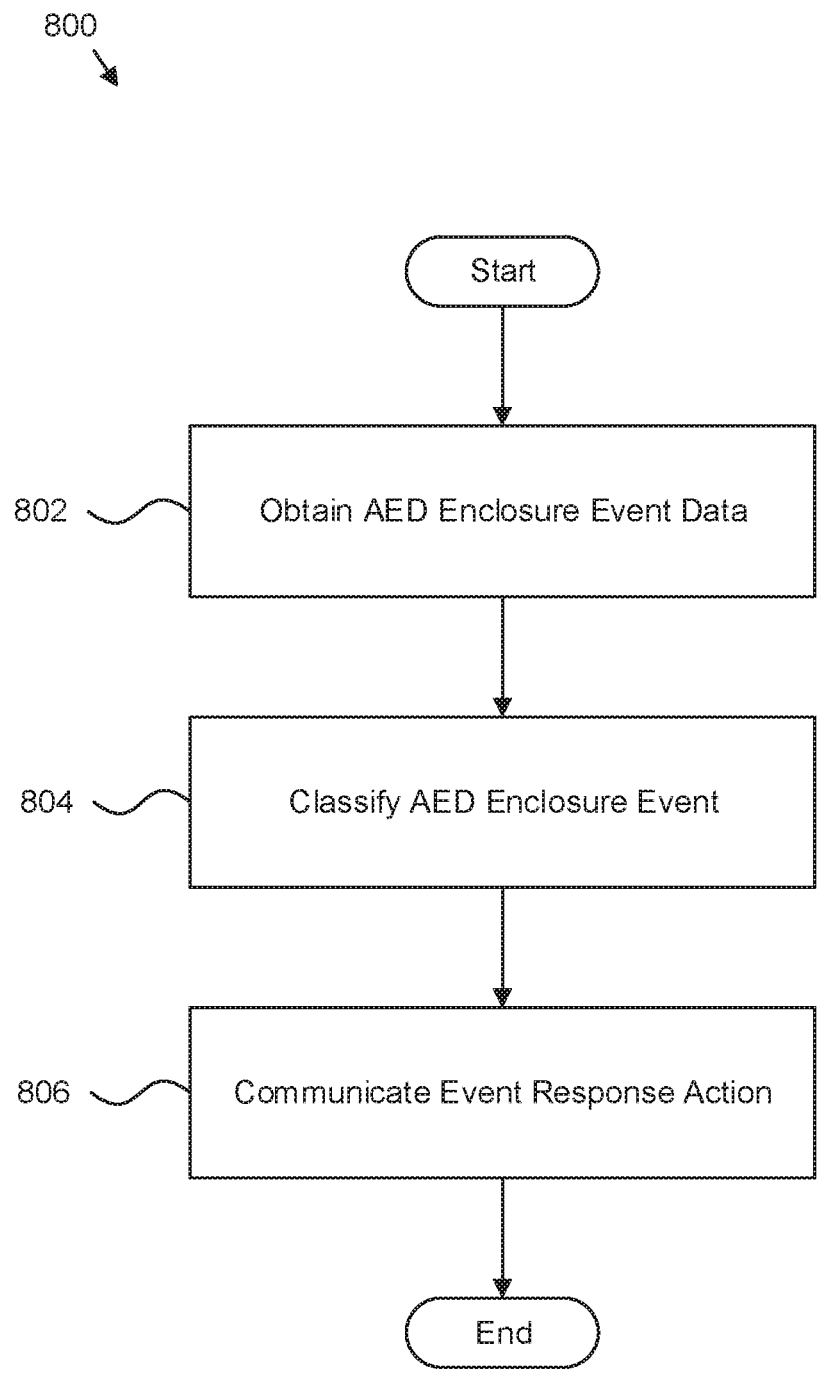
FIG. 8 is a schematic flow chart diagram illustrating one embodiment of a method for independent AED readiness determination for automated external defibrillator deployment.

FIG. 8 is a schematic flow chart diagram illustrating one embodiment of a method 800 for independent AED readiness determination for automated external defibrillator deployment. In one embodiment, the method 800 begins and includes obtaining 802 event data for an automated external defibrillator ("AED") enclosure event, the AED enclosure event corresponding to an AED registered to be disposed within an AED enclosure, classifying 804 the AED enclosure event into a predetermined event category, and communicating 806 a response action, in response to the AED enclosure event. In various embodiments, all or a portion of the steps of the method 800 are performed by an instance of the AED readiness apparatus 104 including the controller 202 and/or the communication interface 204 (e.g., as depicted and described above with respect to the AED readiness apparatuses 304, 404, 504, 604, and 704 illustrated respectively in FIGS. 3, 4, 5 6, and 7).

Figure 9:
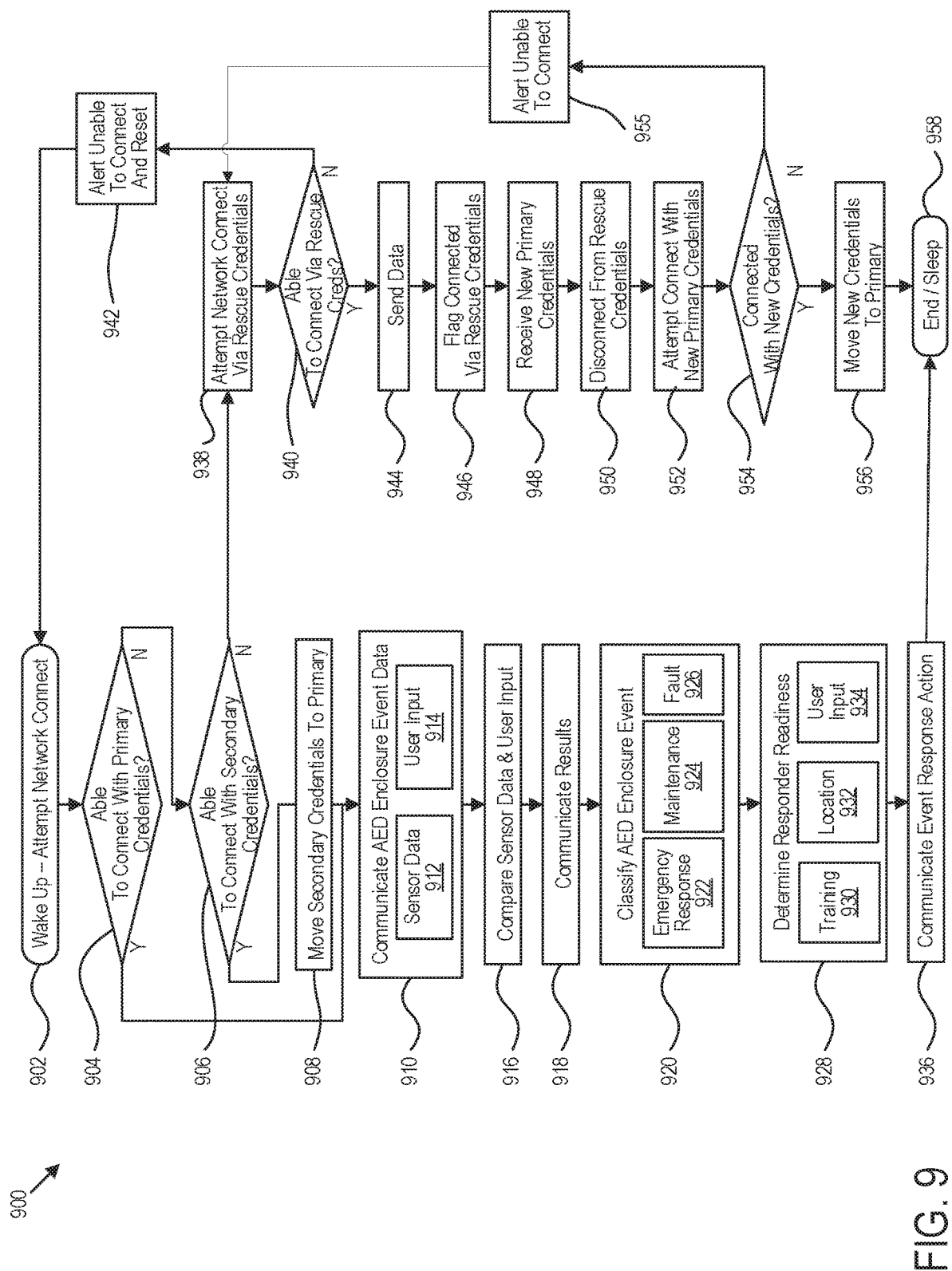
FIG. 9 is a schematic flow chart diagram illustrating another embodiment of a method for an independent AED readiness determination for automated external defibrillator deployment.

FIG. 9 is a schematic flow chart diagram illustrating another embodiment of a method 900 for independent AED readiness determination for AED deployment. In certain embodiments, the method 900 includes waking up 902 to connect to the data network 106 to communication event data for an automated external defibrillator ("AED") enclosure event, where the AED enclosure event corresponds to an AED registered to be disposed within an AED enclosure. As used herein, with regard to certain decision steps such as 904, 906, 940, 954, the terms "time out," "timed out," or similar terms refer to implementations in which whether one or more AED readiness apparatuses are able to connect to the data network is subject to a timeout period. For example, if the AED readiness apparatus is unable to connect within a predetermined time at step 904 using the primary credentials (e.g., 211*a*), it may be referred to as a timed out AED readiness apparatus. In various embodiments, the AED readiness apparatus next attempts 906 to connect using the secondary credentials (e.g., 211*b*) that may be pre-configured by an administrative interface to facilitate easy updating of a fleet of one or more AED readiness apparatuses without having to perform individual manual updates for each AED readiness apparatus. For example, if a network password has been updated during a sleep period of one or more AED readiness apparatuses and secondary credentials have been provided via the administrative interface, then the method 900 connects to the network and moves the secondary credentials to primary so that the on the next wake up 902, the AED readiness apparatus will try first to connect 904 with the new primary credentials.

In response to determining that an AED readiness apparatus is currently unable to connect (e.g., timed out) after attempting to connect via the primary credentials and the secondary credentials, a set of rescue steps 938 through 956 may be taken as described in more detail below. Upon successfully connecting to the data network, the method 900 continues and communicates 910 AED enclosure event data for further processing or display e.g., by a server, a dashboard, an application, and so forth.

In certain embodiments, the event data includes comparing 916 the user input data 914 collected through a user interface and the sensor data 912 collected through one or more sensors that are physically separate from the AED and electrically unconnected to the AED. In some embodiments, the method further includes comparing 916 the user input data 914 and the sensor data 912 and communicating 918 results of the comparison to a mobile communication device and/or to a second communication device. Such a comparison may beneficially assist in determining whether the sensors are operating correctly and/or whether users are aware of and correctly monitoring AED readiness status.

In various embodiments, the method 900 includes classifying 920 the AED enclosure event data into event categories. One example of an AED emergency response event category is an emergency response event 922. An emergency response event can indicate that the AED was removed from the enclosure in response to a medical emergency such as a cardiac arrest. Keeping track of emergency response events may beneficially alert those with responsibility for use and maintenance of the AED to follow up to see whether any consumable supplies such as pads were used or whether the AED functioned as expected during the emergency response.

Another category of AED enclosure event is a maintenance event 924. In some embodiments, tracking maintenance events 924 enables a user to know and have a record of the dates and times that that maintenance of the AED has been performed.

In some embodiments, the method includes communicating 936 a response action to facilitate configuration of the AED enclosure with an updated controller configured to collect the sensor data from at least one of the one or more sensors disposed within the AED enclosure. A third example of an AED enclosure event category is a fault event 926. In certain embodiments, a fault event 926 may indicate a fault in the AED such as a sensor detecting a parameter such as temperature, humidity, battery voltage, and so forth, falling outside of expected operating boundaries. In some embodiments, a fault event 926 may indicate a fault in the AED readiness apparatus such as a battery that has lower than expected charge, or a malfunctioning sensor. In various embodiments, sensing and communicating fault events can be utilized to improve AED readiness.

In certain embodiments, the method 900 further includes determining 928 a responder readiness status such as, for example, a training status 930, a responder location 932, and/or a readiness status indicated by user input 934. Each of these status types may be used to promote awareness and/or improve the training of current or potential future responders. The above examples are merely representative of numerous responder readiness parameters that may be determined and/or communicated by the method 900.

The method 900 continues and, in various embodiments, includes communicating 936 a response action for the detected AED enclosure event. In some embodiments, communicating 936 the response action to the mobile communication device is performed in response to determining that the mobile communication device corresponds to a responder having a readiness status that satisfies one or more predetermined criteria for the predetermined event category. For example, the method may communicate a response action involving more detailed medical terms and actions in response to determining that the responder is a well-trained emergency responder rather than a person with little or no recorded training in AED usage.

In various embodiments, after communicating 936 one or more response actions for the detected AED enclosure event, the method 900 ends or sleeps 958 to reawaken periodically according to a predetermined schedule.

Turning now to the rescue procedure which is depicted in actions 938 through 956 of FIG. 9. In certain embodiments, in response to determining that attempting 906 to connect the AED readiness apparatus to the data network is unsuccessful using either the primary or the secondary credentials, the method 900 attempts 938 to connect to a data network using a rescue procedure and rescue credentials. In such embodiments, a first portion of the AED reading apparatus and/or the rescue module may be implemented in a stationary electronic device positioned with the AED enclosure as depicted in FIG. 2, the rescue credentials may be preconfigured in the code 208 (e.g., firmware for the AED readiness apparatus 104.

For example, the rescue module 218 may temporarily configure a mobile communication device 102 such as a tablet or smart phone as a network access point, also referred to as a "hotspot." For example, in certain embodiments, the mobile communication device 102 acts as a WiFi network to which the AED readiness apparatus temporarily connects, in view of the fact that the AED readiness apparatus was unable to connect to the desired data network 106 either because the primary credentials 211a are no longer valid for that network because the network password was changed to a new password without the secondary credentials 211b having been preconfigured with the new password, or because the access point 109 to which a stationary implementation of an AED readiness apparatus 104, 304, typically connects was out of service at the time of the connection attempt.

In such embodiments, the rescue credentials 211c are preconfigured in firmware in stationary embodiments of the AED readiness apparatus 104, 304 and are similarly preconfigured in a rescue application that is accessible online via the mobile communication device 102 that is acting as the hotspot. By connecting via the hotspot, the AED readiness apparatus can send 944 rescue data, such as updated primary credentials and/or secondary credentials, and may take actions to facilitate network connections going forward. In certain embodiments, the AED readiness apparatus may send certain data such as AED enclosure event data while connected via the rescue credentials and/or may wait to send some AED enclosure event data until the AED readiness apparatus has reestablished connection using updated primary credentials 211a received as part of the rescue procedure.

In some embodiments, the method 900 flags 946 that the network connection was established via the rescue credentials and in response, receives 948 updated credentials for the data network. For example, updated primary credentials 211a (depicted in FIGS. 2 and 6B) may be provided to the rescue procedure e.g., through the administrative interface 602. The method 900 continues and the AED readiness apparatus disconnects 950 from the network using the hotspot and rescue credentials and attempts to connect 952 using the new primary credentials. In response to being able to connect using the new primary credentials provide as part of the rescue procedure, the method 900 may move 956 the new credentials to the memory of the AED readiness apparatus as the primary credential 211a.

In response to not being able to connect with the new primary credentials provided while connected via the rescue credentials, a portion of the rescue process may alert 955 locally (e.g., by sounding a series of beeps, flashing lights, or similar alert actions) that the AED readiness apparatus was unable to connect) after which the method 900 may repeat, i.e., go back to action 938 of the method. Similarly, if the method 900 is unable to connect via the rescue credentials. the AED apparatus may time out, reset, and/or sleep/reawake (e.g., return to step 902) if the AED readiness apparatus is unable to connect via the rescue credentials (e.g., timed out at step 940). In some embodiments, the method 900 may provide an alert 942 (such as a series of audible beeps and/or visible flashes to attract the attention of a person at the place of deployment of the AED readiness apparatus. The alert may signal that the AED readiness apparatus may be due for service.

In various embodiments, all or a portion of the steps of the method 900 are performed by an instance of the AED readiness apparatus 104 including the controller 202 and/or the communication interface 204 (e.g., as depicted and described above with respect to the AED readiness apparatuses 304, 404, 504, 604, and 704 illustrated respectively in FIGS. 3, 4, 5, 6, and 7).

Embodiments may be practiced in other specific forms. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An apparatus comprising:
a controller configured to detect an automated external defibrillator ("AED") enclosure event corresponding to an AED registered to be disposed within an AED enclosure, wherein the controller is configured to communicate data for classifying an AED enclosure event into a predetermined event category; and
a communication interface configured to communicate a response action in response to data of the AED enclosure event satisfying one or more predetermined criteria for the predetermined event category,
wherein the communication interface is configured to periodically awaken and attempt to establish a wireless network connection for communicating AED enclosure event data using one or more credentials of a predetermined series of credentials selected from primary credentials, secondary credentials, and rescue credentials.

2. The apparatus of claim 1, wherein the controller is configured to collect one or more AED readiness parameters selected from:
an individual enclosure identifier for linking the AED enclosure to an individual AED identifier of the AED registered to be disposed within the AED enclosure;
an enclosure access indicator that indicates whether the AED enclosure is open;
an AED-presence indicator that indicates whether the AED is correctly disposed within the AED enclosure;
an audible readiness indicator of the AED;
a visual readiness indicator of the AED; and
a storage environment indicator comprising one or more of temperature, humidity within the AED enclosure.

3. The apparatus of claim 2, wherein the controller is configured to collect the one or more AED readiness parameters using one or more of:
a sensor that is physically separate from and electrically unconnected to the AED; and
a user interface of a mobile communication device.

4. The apparatus of claim 3, wherein the individual enclosure identifier is externally coupled to the AED enclosure, internally stored in a tangible memory, or a combination thereof.

5. The apparatus of claim 3, wherein the sensor is disposed inside the AED enclosure.

6. The apparatus of claim 2, wherein the controller is configured to communicate with an access sensor configured to determine whether an access door of the AED enclosure is open.

7. The apparatus of claim 6, wherein the apparatus is configured to wake the controller from a dormant mode to an active mode in response to the access sensor determining that the access door is open.

8. The apparatus of claim 2, wherein the controller further communicates with an object sensor configured to determine whether the AED is disposed correctly within the AED enclosure.

9. The apparatus of claim 8, wherein the object sensor comprises a time-of-flight sensor configured to measure a reflected signal distance to determine whether the AED is disposed within the AED enclosure.

10. The apparatus of claim 2, wherein the controller communicates with an input transducer configured to collect audio data of the audible readiness indicator.

11. The apparatus of claim 10, further comprising a filter that distinguishes the audible readiness indicator from sounds that fail to satisfy predetermined parameters for the audible readiness indicator.

12. The apparatus of claim 11, wherein the filter performs frequency domain processing and time domain processing on the audio data captured by the input transducer to distinguish the audible readiness indicator from the sounds that fail to satisfy the predetermined parameters for the audible readiness indicator.

13. The apparatus of claim 2, wherein the controller comprises part of a communication device external to the AED enclosure, the communication device comprising a user interface configured to collect the one or more AED readiness parameters through the user interface.

14. A method comprising:
initiating a request for a network connection between a plurality of stationary AED readiness apparatuses and a data network using one or more credentials of a predetermined series of credentials selected from primary credentials, secondary credentials, and rescue credentials for authenticating the plurality of stationary AED readiness apparatuses to the data network; and in response to establishing the network connection between the plurality of stationary AED readiness apparatuses and the data network:
communicating event data for an automated external defibrillator ("AED") enclosure event, the AED enclosure event corresponding to an AED registered to be disposed within an AED enclosure;
classifying the AED enclosure event into a predetermined event category; and
communicating a response action in response to the AED enclosure event.

15. The method of claim 14, wherein the event data comprises user input data collected through a user interface and sensor data collected through one or more sensors that are physically separate from the AED and electrically unconnected to the AED, the method further comprising:
performing a comparison of the user input data and the sensor data; and
communicating results of the comparison to a mobile communication device, a second communication device, or a combination thereof.

16. The method of claim 15, wherein the event data comprises user input data collected through a user interface, the method further comprising communicating the response action to facilitate configuration of the AED enclosure with an updated controller configured to collect the sensor data from at least one of the one or more sensors disposed within the AED enclosure.

17. The method of claim 15, wherein the predetermined event category for the AED enclosure event is selected from an emergency response event, a maintenance event, a fault event, and combinations thereof.

18. The method of claim 17, wherein communicating the response action to the mobile communication device is performed in response to determining that the mobile communication device corresponds to a responder having a readiness status that satisfies one or more predetermined criteria for the predetermined event category.

19. The method of claim 18, further comprising determining the readiness status of the responder based on a parameter selected from a level of training to respond to the AED enclosure event, a location of the mobile communication device corresponding to the responder, a user input indicating the readiness status of the responder, an AED event response history of the responder, and combinations thereof.

20. A computer program product comprising a non-transitory computer readable storage medium having program instructions embodied therewith, wherein the program instructions are executable by a mobile communication device to cause the mobile communication device to:
configure a predetermined series of credentials selected from primary credentials and secondary credentials for attempting to connect a plurality of stationary AED readiness apparatuses to a data network;
configure a mobile communication device as a temporary access point accessible using predetermined rescue credentials for one or more timed out AED readiness apparatuses to communicate one or more updated primary credentials and/or secondary credentials to the timed out AED readiness apparatuses; and
in response to the AED readiness apparatuses connecting to the data network:
obtain event data for an automated external defibrillator ("AED") enclosure event detected by a detector controller, the AED enclosure event corresponding to an AED registered to be disposed within an AED enclosure;
obtain responder data indicating a readiness status for a responder that is a user of the mobile communication device; and
communicate a response action in response to classifying the AED enclosure event into a predetermined event category and determining that the readiness status for the responder satisfies predetermined criteria.

* * * * *